US012651659B2

(12) United States Patent
Narayanaswami

(10) Patent No.: US 12,651,659 B2
(45) Date of Patent: Jun. 9, 2026

(54) INSULIN ADAPTATION AND SAFETY MONITORING FOR SICK DAY MANAGEMENT

(71) Applicant: INSULET CORPORATION, Acton, MA (US)

(72) Inventor: Rangarajan Narayanaswami, Weston, MA (US)

(73) Assignee: INSULET CORPORATION, Acton, MA (US)

( * ) Notice: Subject to any disclaimer, the term of this patent is extended or adjusted under 35 U.S.C. 154(b) by 535 days.

(21) Appl. No.: 18/137,183

(22) Filed: Apr. 20, 2023

(65) Prior Publication Data

US 2023/0338652 A1     Oct. 26, 2023

Related U.S. Application Data

(60) Provisional application No. 63/333,149, filed on Apr. 21, 2022.

(51) Int. Cl.
*G16H 20/10* (2018.01)
*A61B 5/145* (2006.01)
(Continued)

(52) U.S. Cl.
CPC ......... *G16H 20/10* (2018.01); *A61B 5/14532* (2013.01); *A61B 5/14546* (2013.01);
(Continued)

(58) Field of Classification Search
CPC ........ G16H 20/10; G16H 20/30; G16H 20/60; A61B 5/14532; A61B 5/14546; A61M 5/1723; A61M 5/14248; A61M 2202/0486; A61M 2205/52; A61M 2205/502; A61M 2205/3303; A61M 2230/201

See application file for complete search history.

(56) References Cited

U.S. PATENT DOCUMENTS

| | | |
|---|---|---|
| 303,013 A | 8/1884 | Horton |
| 441,663 A | 12/1890 | Hofbauer |

(Continued)

FOREIGN PATENT DOCUMENTS

| | | |
|---|---|---|
| AU | 2015200834 A1 | 3/2015 |
| AU | 2015301146 A1 | 3/2017 |

(Continued)

OTHER PUBLICATIONS

US 5,954,699 A, 09/1999, Jost et al. (withdrawn)
(Continued)

*Primary Examiner* — David P. Olynick
(74) *Attorney, Agent, or Firm* — Goodwin Procter LLP

(57) ABSTRACT

Disclosed are an apparatus, system, processes, and techniques for adapting drug delivery and monitoring a user's safety when the user is experiencing a sick day. A processor may be operable to provide a graphical user interface that presents a sickness mode prompt for a user to indicate that the user or another person with diabetes is sick. The graphical user interface may present symptoms from which a user may select. Based on the selection of symptoms, glucose measurement values, and/or ketone measurement values, a response to the user's indication of sickness may be provided.

9 Claims, 7 Drawing Sheets

400

410 — Receive a sickness indication that a user is experiencing a sickness

420 — Receive a ketone measurement value from a ketone sensor

430 — Receive a blood glucose measurement value from a blood glucose sensor

440 — Determine whether the received blood glucose measurement value is within a predetermined blood glucose value range 450 — Based on the sickness indication, the determination of whether the received blood glucose measurement value is within a predetermined blood glucose value range, and based on the ketone measurement value, modify a medication delivery algorithm setting 460 — Determine an adjustment in medication delivery according to the modified medication delivery algorithm setting

(51) Int. Cl.
   *A61M 5/142*        (2006.01)
   *A61M 5/172*        (2006.01)
(52) U.S. Cl.
   CPC ....... *A61M 5/1723* (2013.01); *A61M 5/14248*
     (2013.01); *A61M 2202/0486* (2013.01); *A61M 2205/3303* (2013.01); *A61M 2205/502* (2013.01); *A61M 2205/52* (2013.01); *A61M 2230/201* (2013.01)

(56)                References Cited

U.S. PATENT DOCUMENTS

|           |   |         |                     |
|-----------|---|---------|---------------------|
| 445,545   | A | 2/1891  | Crane               |
| 588,583   | A | 8/1897  | Lade                |
| 955,911   | A | 4/1910  | Saegmuller          |
| 1,441,508 | A | 1/1923  | Marius              |
| 2,283,925 | A | 5/1942  | Harvey              |
| 2,797,149 | A | 6/1957  | Skeggs              |
| 2,886,529 | A | 5/1959  | Guillaud            |
| 3,574,114 | A | 4/1971  | Monforte            |
| 3,614,554 | A | 10/1971 | Shield              |
| 3,631,847 | A | 1/1972  | Hobbs               |
| 3,634,039 | A | 1/1972  | Brondy              |
| 3,812,843 | A | 5/1974  | Wootten et al.      |
| 3,841,328 | A | 10/1974 | Jensen              |
| 3,885,662 | A | 5/1975  | Schaefer            |
| 3,963,380 | A | 6/1976  | Thomas, Jr. et al.  |
| 3,983,077 | A | 9/1976  | Fuller et al.       |
| 4,055,175 | A | 10/1977 | Clemens et al.      |
| 4,108,177 | A | 8/1978  | Pistor              |
| 4,146,029 | A | 3/1979  | Ellinwood, Jr.      |
| 4,151,845 | A | 5/1979  | Clemens             |
| 4,206,401 | A | 6/1980  | Meyer               |
| 4,245,634 | A | 1/1981  | Albisser et al.     |
| 4,268,150 | A | 5/1981  | Chen                |
| 4,277,226 | A | 7/1981  | Archibald           |
| 4,307,713 | A | 12/1981 | Galkin et al.       |
| 4,313,439 | A | 2/1982  | Babb et al.         |
| 4,368,980 | A | 1/1983  | Aldred et al.       |
| 4,373,527 | A | 2/1983  | Fischell            |
| 4,398,542 | A | 8/1983  | Cunningham et al.   |
| 4,400,683 | A | 8/1983  | Eda et al.          |
| 4,403,984 | A | 9/1983  | Ash et al.          |
| 4,424,720 | A | 1/1984  | Bucchianeri         |
| 4,435,173 | A | 3/1984  | Siposs et al.       |
| 4,464,170 | A | 8/1984  | Clemens et al.      |
| 4,469,481 | A | 9/1984  | Kobayashi           |
| 4,475,901 | A | 10/1984 | Kraegen et al.      |
| 4,498,843 | A | 2/1985  | Schneider et al.    |
| 4,507,115 | A | 3/1985  | Kambara et al.      |
| 4,523,170 | A | 6/1985  | Huth, III           |
| 4,526,568 | A | 7/1985  | Clemens et al.      |
| 4,526,569 | A | 7/1985  | Bernardi            |
| 4,529,401 | A | 7/1985  | Leslie et al.       |
| 4,551,134 | A | 11/1985 | Slavik et al.       |
| 4,559,033 | A | 12/1985 | Stephen et al.      |
| 4,559,037 | A | 12/1985 | Franetzki et al.    |
| 4,560,979 | A | 12/1985 | Rosskopf            |
| 4,562,751 | A | 1/1986  | Nason et al.        |
| 4,573,968 | A | 3/1986  | Parker              |
| 4,585,439 | A | 4/1986  | Michel              |
| 4,587,850 | A | 5/1986  | Moser               |
| 4,601,707 | A | 7/1986  | Albisser et al.     |
| 4,624,661 | A | 11/1986 | Arimond             |
| 4,633,878 | A | 1/1987  | Bombardieri         |
| 4,634,427 | A | 1/1987  | Hannula et al.      |
| 4,646,038 | A | 2/1987  | Wanat               |
| 4,657,529 | A | 4/1987  | Prince et al.       |
| 4,678,408 | A | 7/1987  | Nason et al.        |
| 4,684,368 | A | 8/1987  | Kenyon              |
| 4,685,903 | A | 8/1987  | Cable et al.        |
| 4,731,726 | A | 3/1988  | Allen, III          |
| 4,743,243 | A | 5/1988  | Vaillancourt        |
| 4,755,169 | A | 7/1988  | Sarnoff et al.      |
| 4,755,173 | A | 7/1988  | Konopka et al.      |
| 4,759,120 | A | 7/1988  | Bernstein           |
| 4,781,688 | A | 11/1988 | Thoma et al.        |
| 4,781,693 | A | 11/1988 | Martinez et al.     |
| 4,801,957 | A | 1/1989  | Vandemoere          |
| 4,808,161 | A | 2/1989  | Kamen               |
| 4,836,752 | A | 6/1989  | Burkett             |
| 4,850,954 | A | 7/1989  | Charvin             |
| 4,854,170 | A | 8/1989  | Brimhall et al.     |
| 4,859,492 | A | 8/1989  | Rogers, Jr. et al.  |
| 4,880,770 | A | 11/1989 | Mir et al.          |
| 4,882,600 | A | 11/1989 | Van de Moere        |
| 4,886,499 | A | 12/1989 | Cirelli et al.      |
| 4,898,578 | A | 2/1990  | Rubalcaba, Jr.      |
| 4,898,579 | A | 2/1990  | Groshong et al.     |
| 4,900,292 | A | 2/1990  | Berry et al.        |
| 4,919,596 | A | 4/1990  | Slate et al.        |
| 4,925,444 | A | 5/1990  | Orkin et al.        |
| 4,940,527 | A | 7/1990  | Kazlauskas et al.   |
| 4,944,659 | A | 7/1990  | Labbe et al.        |
| 4,961,055 | A | 10/1990 | Habib et al.        |
| 4,967,201 | A | 10/1990 | Rich, III           |
| 4,969,874 | A | 11/1990 | Michel et al.       |
| 4,973,998 | A | 11/1990 | Gates               |
| 4,975,581 | A | 12/1990 | Robinson et al.     |
| 4,976,720 | A | 12/1990 | Machold et al.      |
| 4,981,140 | A | 1/1991  | Wyatt               |
| 4,994,047 | A | 2/1991  | Walker et al.       |
| 5,007,286 | A | 4/1991  | Malcolm et al.      |
| 5,007,458 | A | 4/1991  | Marcus et al.       |
| 5,045,871 | A | 9/1991  | Reinholdson         |
| 5,062,841 | A | 11/1991 | Siegel              |
| 5,084,749 | A | 1/1992  | Losee et al.        |
| 5,097,834 | A | 3/1992  | Skrabal             |
| 5,102,406 | A | 4/1992  | Arnold              |
| 5,109,850 | A | 5/1992  | Blanco et al.       |
| 5,125,415 | A | 6/1992  | Bell                |
| 5,130,675 | A | 7/1992  | Sugawara            |
| 5,134,079 | A | 7/1992  | Cusack et al.       |
| 5,139,999 | A | 8/1992  | Gordon et al.       |
| 5,153,827 | A | 10/1992 | Coutre et al.       |
| 5,154,973 | A | 10/1992 | Imagawa et al.      |
| 5,165,406 | A | 11/1992 | Wong                |
| 5,176,662 | A | 1/1993  | Bartholomew et al.  |
| 5,178,609 | A | 1/1993  | Ishikawa            |
| 5,189,609 | A | 2/1993  | Tivig et al.        |
| 5,198,824 | A | 3/1993  | Poradish            |
| 5,205,819 | A | 4/1993  | Ross et al.         |
| 5,207,642 | A | 5/1993  | Orkin et al.        |
| 5,213,483 | A | 5/1993  | Flaherty et al.     |
| 5,217,754 | A | 6/1993  | Santiago-Aviles et al. |
| 5,219,377 | A | 6/1993  | Poradish            |
| 5,232,439 | A | 8/1993  | Campbell et al.     |
| 5,237,993 | A | 8/1993  | Skrabal             |
| 5,239,326 | A | 8/1993  | Takai               |
| 5,244,463 | A | 9/1993  | Cordner, Jr. et al. |
| 5,254,096 | A | 10/1993 | Rondelet et al.     |
| 5,257,980 | A | 11/1993 | Van Antwerp et al.  |
| 5,261,882 | A | 11/1993 | Sealfon             |
| 5,263,198 | A | 11/1993 | Geddes et al.       |
| 5,272,485 | A | 12/1993 | Mason et al.        |
| 5,273,517 | A | 12/1993 | Barone et al.       |
| 5,281,202 | A | 1/1994  | Weber et al.        |
| 5,281,808 | A | 1/1994  | Kunkel              |
| 5,299,571 | A | 4/1994  | Mastrototaro        |
| 5,308,982 | A | 5/1994  | Ivaldi et al.       |
| 5,342,298 | A | 8/1994  | Michaels et al.     |
| 5,346,476 | A | 9/1994  | Elson               |
| 5,364,342 | A | 11/1994 | Beuchat et al.      |
| 5,377,674 | A | 1/1995  | Kuestner            |
| 5,380,665 | A | 1/1995  | Cusack et al.       |
| 5,385,539 | A | 1/1995  | Maynard             |
| 5,389,078 | A | 2/1995  | Zalesky             |
| 5,403,797 | A | 4/1995  | Ohtani et al.       |
| 5,411,889 | A | 5/1995  | Hoots et al.        |
| 5,421,812 | A | 6/1995  | Langley et al.      |
| 5,427,988 | A | 6/1995  | Sengupta et al.     |
| 5,433,710 | A | 7/1995  | VanAntwerp et al.   |
| 5,452,033 | A | 9/1995  | Balling et al.      |
| 5,456,945 | A | 10/1995 | McMillan et al.     |

(56) References Cited

U.S. PATENT DOCUMENTS

| | | | |
|---|---|---|---|
| 5,468,727 A | 11/1995 | Phillips et al. |
| 5,478,610 A | 12/1995 | Desu et al. |
| 5,505,709 A | 4/1996 | Funderburk et al. |
| 5,505,828 A | 4/1996 | Wong et al. |
| 5,507,288 A | 4/1996 | Bocker et al. |
| 5,513,382 A | 4/1996 | Agahi-Kesheh et al. |
| 5,533,389 A | 7/1996 | Kamen et al. |
| 5,535,445 A | 7/1996 | Gunton |
| 5,540,772 A | 7/1996 | McMillan et al. |
| 5,543,773 A | 8/1996 | Evans et al. |
| 5,558,640 A | 9/1996 | Pfeiler et al. |
| 5,563,584 A | 10/1996 | Rader et al. |
| 5,569,186 A | 10/1996 | Lord et al. |
| 5,576,781 A | 11/1996 | Deleeuw |
| 5,582,593 A | 12/1996 | Hultman |
| 5,584,053 A | 12/1996 | Kommrusch et al. |
| 5,584,813 A | 12/1996 | Livingston et al. |
| 5,585,733 A | 12/1996 | Paglione |
| 5,586,553 A | 12/1996 | Halili et al. |
| 5,590,387 A | 12/1996 | Schmidt et al. |
| 5,609,572 A | 3/1997 | Lang |
| 5,614,252 A | 3/1997 | McMillan et al. |
| 5,625,365 A | 4/1997 | Tom et al. |
| 5,635,433 A | 6/1997 | Sengupta |
| 5,637,095 A | 6/1997 | Nason et al. |
| 5,647,853 A | 7/1997 | Feldmann et al. |
| 5,660,163 A | 8/1997 | Schulman et al. |
| 5,665,065 A | 9/1997 | Colman et al. |
| 5,665,070 A | 9/1997 | McPhee |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,707,459 A | 1/1998 | Itoyama et al. |
| 5,707,715 A | 1/1998 | deRochemont et al. |
| 5,713,875 A | 2/1998 | Tanner, II |
| 5,714,123 A | 2/1998 | Sohrab |
| 5,716,343 A | 2/1998 | Kriesel et al. |
| 5,722,397 A | 3/1998 | Eppstein |
| 5,726,404 A | 3/1998 | Brody |
| 5,726,751 A | 3/1998 | Altendorf et al. |
| 5,741,228 A | 4/1998 | Lambrecht et al. |
| 5,746,217 A | 5/1998 | Erickson et al. |
| 5,747,350 A | 5/1998 | Sattler |
| 5,747,870 A | 5/1998 | Pedder |
| 5,748,827 A | 5/1998 | Holl et al. |
| 5,755,682 A | 5/1998 | Knudson et al. |
| 5,758,643 A | 6/1998 | Wong et al. |
| 5,759,923 A | 6/1998 | McMillan et al. |
| 5,764,189 A | 6/1998 | Lohninger |
| 5,771,567 A | 6/1998 | Pierce et al. |
| 5,776,103 A | 7/1998 | Kriesel et al. |
| 5,779,676 A | 7/1998 | Kriesel et al. |
| 5,785,681 A | 7/1998 | Indravudh et al. |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,807,075 A | 9/1998 | Jacobsen et al. |
| 5,817,007 A | 10/1998 | Fodgaard et al. |
| 5,820,622 A | 10/1998 | Gross et al. |
| 5,823,951 A | 10/1998 | Messerschmidt |
| 5,830,999 A | 11/1998 | Dunn |
| 5,839,467 A | 11/1998 | Saaski et al. |
| 5,840,020 A | 11/1998 | Heinonen et al. |
| 5,848,991 A | 12/1998 | Gross et al. |
| 5,851,197 A | 12/1998 | Marano et al. |
| 5,854,608 A | 12/1998 | Leisten |
| 5,858,005 A | 1/1999 | Kriesel |
| 5,858,239 A | 1/1999 | Kenley et al. |
| 5,859,621 A | 1/1999 | Leisten |
| 5,865,806 A | 2/1999 | Howell |
| 5,867,688 A | 2/1999 | Simmon et al. |
| 5,871,470 A | 2/1999 | McWha |
| 5,879,310 A | 3/1999 | Sopp et al. |
| 5,889,459 A | 3/1999 | Hattori et al. |
| 5,891,097 A | 4/1999 | Saito et al. |
| 5,892,489 A | 4/1999 | Kanba et al. |
| 5,897,530 A | 4/1999 | Jackson |
| 5,899,882 A | 5/1999 | Waksman et al. |
| 5,902,253 A | 5/1999 | Pfeiffer et al. |
| 5,903,421 A | 5/1999 | Furutani et al. |
| 5,906,597 A | 5/1999 | McPhee |
| 5,911,716 A | 6/1999 | Rake et al. |
| 5,919,167 A | 7/1999 | Mulhauser et al. |
| 5,931,814 A | 8/1999 | Alex et al. |
| 5,932,175 A | 8/1999 | Knute et al. |
| 5,933,121 A | 8/1999 | Rainhart et al. |
| 5,935,099 A | 8/1999 | Peterson et al. |
| 5,945,963 A | 8/1999 | Leisten |
| 5,947,911 A | 9/1999 | Wong et al. |
| 5,957,890 A | 9/1999 | Mann et al. |
| 5,961,492 A | 10/1999 | Kriesel et al. |
| 5,965,848 A | 10/1999 | Altschul et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,019,747 A | 2/2000 | McPhee |
| 6,023,251 A | 2/2000 | Koo et al. |
| 6,024,539 A | 2/2000 | Blomquist |
| 6,027,826 A | 2/2000 | deRochemont et al. |
| 6,028,568 A | 2/2000 | Asakura et al. |
| 6,031,445 A | 2/2000 | Marty et al. |
| 6,032,059 A | 2/2000 | Henning et al. |
| 6,036,924 A | 3/2000 | Simons et al. |
| 6,040,578 A | 3/2000 | Malin et al. |
| 6,040,805 A | 3/2000 | Huynh et al. |
| 6,046,707 A | 4/2000 | Gaughan et al. |
| 6,049,727 A | 4/2000 | Crothall |
| 6,050,978 A | 4/2000 | Orr et al. |
| 6,052,040 A | 4/2000 | Hino |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,111,544 A | 8/2000 | Dakeya et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,143,432 A | 11/2000 | de Rochemont et al. |
| 6,154,176 A | 11/2000 | Fathy et al. |
| 6,157,041 A | 12/2000 | Thomas et al. |
| 6,161,028 A | 12/2000 | Braig et al. |
| 6,162,639 A | 12/2000 | Douglas |
| 6,171,264 B1 | 1/2001 | Bader |
| 6,174,300 B1 | 1/2001 | Kriesel et al. |
| 6,176,004 B1 | 1/2001 | Rainhart et al. |
| 6,181,297 B1 | 1/2001 | Leisten |
| 6,188,368 B1 | 2/2001 | Koriyama et al. |
| 6,190,359 B1 | 2/2001 | Heruth |
| 6,195,049 B1 | 2/2001 | Kim et al. |
| 6,196,046 B1 | 3/2001 | Braig et al. |
| 6,200,287 B1 | 3/2001 | Keller et al. |
| 6,200,293 B1 | 3/2001 | Kriesel et al. |
| 6,200,338 B1 | 3/2001 | Solomon et al. |
| 6,204,203 B1 | 3/2001 | Narwankar et al. |
| 6,208,843 B1 | 3/2001 | Huang et al. |
| 6,214,629 B1 | 4/2001 | Freitag et al. |
| 6,222,489 B1 | 4/2001 | Tsuru et al. |

(56)  References Cited

U.S. PATENT DOCUMENTS

| | | |
|---|---|---|
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,266,020 B1 | 7/2001 | Chang |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,300,894 B1 | 10/2001 | Lynch et al. |
| 6,309,370 B1 | 10/2001 | Haim et al. |
| 6,312,888 B1 | 11/2001 | Wong et al. |
| 6,320,547 B1 | 11/2001 | Fathy et al. |
| 6,323,549 B1 | 11/2001 | deRochemont et al. |
| 6,334,851 B1 | 1/2002 | Hayes et al. |
| 6,363,609 B1 | 4/2002 | Pickren |
| 6,375,627 B1 | 4/2002 | Mauze et al. |
| 6,375,638 B2 | 4/2002 | Nason et al. |
| 6,379,301 B1 | 4/2002 | Worthington et al. |
| 6,381,029 B1 | 4/2002 | Tipirneni |
| 6,399,745 B1 | 6/2002 | Ertl |
| 6,402,689 B1 | 6/2002 | Scarantino et al. |
| 6,468,242 B1 * | 10/2002 | Wilson .................. A61M 5/172 |
| | | 604/65 |
| 6,470,279 B1 | 10/2002 | Samsoondar |
| 6,474,219 B2 | 11/2002 | Klitmose et al. |
| 6,475,196 B1 | 11/2002 | Vachon |
| 6,477,065 B2 | 11/2002 | Parks |
| 6,477,901 B1 | 11/2002 | Tadigadapa et al. |
| 6,484,044 B1 | 11/2002 | Lilienfeld-Toal |
| 6,485,461 B1 | 11/2002 | Mason et al. |
| 6,485,462 B1 | 11/2002 | Kriesel |
| 6,491,656 B1 | 12/2002 | Morris |
| 6,492,949 B1 | 12/2002 | Breglia et al. |
| 6,496,149 B1 | 12/2002 | Birnbaum et al. |
| 6,501,415 B1 | 12/2002 | Viana et al. |
| 6,512,937 B2 | 1/2003 | Blank et al. |
| 6,520,936 B1 | 2/2003 | Mann |
| 6,525,509 B1 | 2/2003 | Petersson et al. |
| 6,527,744 B1 | 3/2003 | Kriesel et al. |
| 6,528,809 B1 | 3/2003 | Thomas et al. |
| 6,537,249 B2 | 3/2003 | Kriesell et al. |
| 6,540,260 B1 | 4/2003 | Tan |
| 6,540,672 B1 | 4/2003 | Simonsen et al. |
| 6,541,820 B1 | 4/2003 | Bol |
| 6,544,212 B2 | 4/2003 | Galley et al. |
| 6,546,268 B1 | 4/2003 | Ishikawa et al. |
| 6,546,269 B1 | 4/2003 | Kurnik |
| 6,552,693 B1 | 4/2003 | Leisten |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,559,735 B1 | 5/2003 | Hoang et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,115 B1 | 5/2003 | Barker et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,583,699 B2 | 6/2003 | Yokoyama |
| 6,595,956 B1 | 7/2003 | Gross et al. |
| 6,605,151 B1 | 8/2003 | Wessels et al. |
| 6,611,419 B1 | 8/2003 | Chakravorty |
| 6,618,603 B2 | 9/2003 | Varalli et al. |
| 6,620,750 B2 | 9/2003 | Kim et al. |
| 6,633,772 B2 | 10/2003 | Ford et al. |
| 6,635,958 B2 | 10/2003 | Bates et al. |
| 6,639,556 B2 | 10/2003 | Baba |
| 6,642,908 B2 | 11/2003 | Pleva et al. |
| 6,645,142 B2 | 11/2003 | Braig et al. |
| 6,650,303 B2 | 11/2003 | Kim et al. |
| 6,653,091 B1 | 11/2003 | Dunn et al. |
| 6,656,158 B2 | 12/2003 | Mahoney et al. |
| 6,662,030 B2 | 12/2003 | Khalil et al. |
| 6,669,663 B1 | 12/2003 | Thompson |
| 6,670,497 B2 | 12/2003 | Tashino et al. |
| 6,678,542 B2 | 1/2004 | Braig et al. |
| 6,680,700 B2 | 1/2004 | Hilgers |
| 6,683,576 B2 | 1/2004 | Achim |
| 6,685,452 B2 | 2/2004 | Christiansen et al. |
| 6,686,406 B2 | 2/2004 | Tomomatsu et al. |
| 6,690,336 B1 | 2/2004 | Leisten et al. |
| 6,697,605 B1 | 2/2004 | Atokawa et al. |
| 6,699,218 B2 | 3/2004 | Flaherty et al. |
| 6,699,221 B2 | 3/2004 | Vaillancourt |
| 6,718,189 B2 | 4/2004 | Rohrscheib et al. |
| 6,720,926 B2 | 4/2004 | Killen et al. |
| 6,721,582 B2 | 4/2004 | Trepagnier et al. |
| 6,723,072 B2 | 4/2004 | Flaherty et al. |
| 6,727,785 B2 | 4/2004 | Killen et al. |
| 6,728,560 B2 | 4/2004 | Kollias et al. |
| 6,731,244 B2 | 5/2004 | Killen et al. |
| 6,731,248 B2 | 5/2004 | Killen et al. |
| 6,733,890 B2 | 5/2004 | Imanaka et al. |
| 6,740,059 B2 | 5/2004 | Flaherty |
| 6,740,072 B2 | 5/2004 | Starkweather et al. |
| 6,741,148 B2 | 5/2004 | Killen et al. |
| 6,742,249 B2 | 6/2004 | deRochemont et al. |
| 6,743,744 B1 | 6/2004 | Kim et al. |
| 6,750,740 B2 | 6/2004 | Killen et al. |
| 6,750,820 B2 | 6/2004 | Killen et al. |
| 6,751,490 B2 | 6/2004 | Esenaliev et al. |
| 6,753,745 B2 | 6/2004 | Killen et al. |
| 6,753,814 B2 | 6/2004 | Killen et al. |
| 6,758,835 B2 | 7/2004 | Close et al. |
| 6,762,237 B2 | 7/2004 | Glatkowski et al. |
| 6,768,319 B2 | 7/2004 | Wang |
| 6,780,156 B2 | 8/2004 | Haueter et al. |
| 6,787,181 B2 | 9/2004 | Uchiyama et al. |
| 6,791,496 B1 | 9/2004 | Killen et al. |
| 6,810,290 B2 | 10/2004 | Lebel et al. |
| 6,826,031 B2 | 11/2004 | Nagai et al. |
| 6,830,558 B2 | 12/2004 | Flaherty et al. |
| 6,830,623 B2 | 12/2004 | Hayashi et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,853,288 B2 | 2/2005 | Ahn et al. |
| 6,858,892 B2 | 2/2005 | Yamagata |
| 6,862,534 B2 | 3/2005 | Sterling et al. |
| 6,864,848 B2 | 3/2005 | Sievenpiper |
| 6,865,408 B1 | 3/2005 | Abbink et al. |
| 6,871,396 B2 | 3/2005 | Sugaya et al. |
| 6,878,871 B2 | 4/2005 | Scher et al. |
| 6,883,778 B1 | 4/2005 | Newton et al. |
| 6,890,291 B2 | 5/2005 | Robinson et al. |
| 6,900,016 B1 | 5/2005 | Venter |
| 6,905,989 B2 | 6/2005 | Ellis et al. |
| 6,906,674 B2 | 6/2005 | McKinzie, III et al. |
| 6,914,566 B2 | 7/2005 | Beard |
| 6,919,119 B2 | 7/2005 | Kalkan et al. |
| 6,928,298 B2 | 8/2005 | Furutani et al. |
| 6,936,029 B2 | 8/2005 | Mann et al. |
| 6,943,430 B2 | 9/2005 | Kwon |
| 6,943,731 B2 | 9/2005 | Killen et al. |
| 6,949,081 B1 | 9/2005 | Chance |
| 6,958,809 B2 | 10/2005 | Sterling et al. |
| 6,963,259 B2 | 11/2005 | Killen et al. |
| 6,989,891 B2 | 1/2006 | Braig et al. |
| 6,990,366 B2 | 1/2006 | Say et al. |
| 7,002,436 B2 | 2/2006 | Ma et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |

(56) References Cited

U.S. PATENT DOCUMENTS

| 7,043,288 B2 | 5/2006 | Davis, III et al. |
| 7,047,637 B2 | 5/2006 | deRochemont et al. |
| 7,060,059 B2 | 6/2006 | Keith et al. |
| 7,060,350 B2 | 6/2006 | Takaya et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,116,949 B2 | 10/2006 | Irie et al. |
| 7,128,727 B2 | 10/2006 | Flaherty et al. |
| 7,137,694 B2 | 11/2006 | Ferran et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,160,272 B1 | 1/2007 | Eyal et al. |
| 7,171,252 B1 | 1/2007 | Scarantino et al. |
| 7,182,726 B2 | 2/2007 | Williams et al. |
| 7,190,988 B2 | 3/2007 | Say et al. |
| 7,204,823 B2 | 4/2007 | Estes et al. |
| 7,230,316 B2 | 6/2007 | Yamazaki et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,291,782 B2 | 11/2007 | Sager et al. |
| 7,303,073 B2 | 12/2007 | Raynal-Olive et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,405,698 B2 | 7/2008 | de Rochemont |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,522,124 B2 | 4/2009 | Smith et al. |
| 7,547,281 B2 | 6/2009 | Hayes et al. |
| 7,553,512 B2 | 6/2009 | Kodas et al. |
| 7,564,887 B2 | 7/2009 | Wang et al. |
| 7,569,030 B2 | 8/2009 | Lebel et al. |
| 7,595,623 B2 | 9/2009 | Bennett |
| 7,608,042 B2 | 10/2009 | Goldberger et al. |
| 7,651,845 B2 | 1/2010 | Doyle, III et al. |
| 7,652,901 B2 | 1/2010 | Kirchmeier et al. |
| 7,680,529 B2 | 3/2010 | Kroll |
| 7,714,794 B2 | 5/2010 | Tavassoli Hozouri |
| 7,734,323 B2 | 6/2010 | Blomquist et al. |
| 7,763,917 B2 | 7/2010 | de Rochemont |
| 7,766,829 B2 | 8/2010 | Sloan et al. |
| 7,771,391 B2 | 8/2010 | Carter |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,812,774 B2 | 10/2010 | Friman et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,056,719 B2 | 11/2011 | Porret et al. |
| 8,066,805 B2 | 11/2011 | Zurcher et al. |
| 8,069,690 B2 | 12/2011 | DeSantolo et al. |
| 8,105,282 B2 | 1/2012 | Susi et al. |
| 8,114,489 B2 | 2/2012 | Nemat-Nasser et al. |
| 8,178,457 B2 | 5/2012 | de Rochemont |
| 8,193,873 B2 | 6/2012 | Kato et al. |
| 8,221,345 B2 | 7/2012 | Blomquist |
| 8,251,907 B2 | 8/2012 | Sterling et al. |
| 8,267,921 B2 | 9/2012 | Yodfat et al. |
| 8,285,487 B2 | 10/2012 | Bergstrom et al. |
| 8,350,657 B2 | 1/2013 | deRochemont |
| 8,354,294 B2 | 1/2013 | De Rochemont et al. |
| 8,449,524 B2 | 5/2013 | Braig et al. |
| 8,452,359 B2 | 5/2013 | Rebec et al. |
| 8,454,557 B1 | 6/2013 | Qi et al. |
| 8,454,576 B2 | 6/2013 | Mastrototaro et al. |
| 8,461,561 B2 | 6/2013 | Freeman et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,593,819 B2 | 11/2013 | de Rochemont |
| 8,597,274 B2 | 12/2013 | Sloan et al. |
| 8,622,954 B2 * | 1/2014 | Shahmirian ............ G16H 20/17 |
| | | 600/347 |
| 8,622,988 B2 | 1/2014 | Hayter |
| 8,715,839 B2 | 5/2014 | de Rochemont |
| 8,727,117 B2 | 5/2014 | Maasarani |
| 8,810,394 B2 | 8/2014 | Kalpin |
| 8,818,782 B2 | 8/2014 | Thukral et al. |
| 8,920,628 B2 | 12/2014 | Gerber |
| 8,939,935 B2 | 1/2015 | OConnor et al. |
| 9,005,166 B2 | 4/2015 | Uber, III et al. |
| 9,061,097 B2 | 6/2015 | Holt et al. |
| 9,171,343 B1 | 10/2015 | Fischell et al. |
| 9,180,244 B2 | 11/2015 | Anderson et al. |
| 9,192,716 B2 | 11/2015 | Jugl et al. |
| 9,233,204 B2 | 1/2016 | Booth et al. |
| 9,248,229 B2 | 2/2016 | Devouassoux et al. |
| 9,402,950 B2 | 8/2016 | Dilanni et al. |
| 9,427,710 B2 | 8/2016 | Jansen |
| 9,486,571 B2 | 11/2016 | Rosinko |
| 9,520,649 B2 | 12/2016 | de Rochemont |
| 9,579,456 B2 | 2/2017 | Budiman et al. |
| 9,598,195 B2 | 3/2017 | Deutschle et al. |
| 9,656,017 B2 | 5/2017 | Greene |
| 9,743,224 B2 | 8/2017 | San Vicente et al. |
| 9,857,090 B2 | 1/2018 | Golden et al. |
| 9,862,519 B2 | 1/2018 | Deutschle et al. |
| 9,907,515 B2 | 3/2018 | Doyle, III et al. |
| 9,974,903 B1 | 5/2018 | Davis et al. |
| 9,980,140 B1 | 5/2018 | Spencer et al. |
| 9,984,773 B2 | 5/2018 | Gondhalekar et al. |
| 10,046,114 B1 | 8/2018 | Biederman et al. |
| 10,080,840 B2 | 9/2018 | Gescheit et al. |
| 10,086,131 B2 | 10/2018 | Okihara |
| 10,248,839 B2 | 4/2019 | Levy et al. |
| 10,335,464 B1 | 7/2019 | Michelich et al. |
| 10,342,926 B2 | 7/2019 | Nazzaro et al. |
| 10,441,717 B2 | 10/2019 | Schmid et al. |
| 10,583,250 B2 | 3/2020 | Mazlish et al. |
| 10,736,548 B2 | 8/2020 | Ahmad et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 11,538,587 B2 | 12/2022 | Bill |
| 12,226,239 B2 | 2/2025 | Williams |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0048969 A1 | 12/2001 | Constantino et al. |
| 2001/0051377 A1 | 12/2001 | Hammer et al. |
| 2001/0053895 A1 | 12/2001 | Vaillancourt |
| 2001/0056258 A1 | 12/2001 | Evans |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0032374 A1 | 3/2002 | Holker et al. |
| 2002/0040208 A1 | 4/2002 | Flaherty et al. |
| 2002/0047768 A1 | 4/2002 | Duffy |
| 2002/0070983 A1 | 6/2002 | Kozub et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2002/0161307 A1 | 10/2002 | Yu et al. |
| 2002/0173769 A1 | 11/2002 | Gray et al. |
| 2002/0190818 A1 | 12/2002 | Endou et al. |
| 2003/0023148 A1 | 1/2003 | Lorenz et al. |

(56) References Cited

U.S. PATENT DOCUMENTS

| | | |
|---|---|---|
| 2003/0034124 A1 | 2/2003 | Sugaya et al. |
| 2003/0040715 A1 | 2/2003 | DAntonio et al. |
| 2003/0050621 A1 | 3/2003 | Lebel et al. |
| 2003/0060692 A1 | 3/2003 | L. Ruchti et al. |
| 2003/0073952 A1 | 4/2003 | Flaherty et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0122647 A1 | 7/2003 | Ou |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0148024 A1 | 8/2003 | Kodas et al. |
| 2003/0163097 A1 | 8/2003 | Fleury et al. |
| 2003/0163789 A1* | 8/2003 | Blomquist ............ A61M 5/142 |
| | | 715/234 |
| 2003/0170436 A1 | 9/2003 | Sumi et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2003/0221621 A1 | 12/2003 | Pokharna et al. |
| 2004/0010207 A1 | 1/2004 | Flaherty et al. |
| 2004/0010507 A1 | 1/2004 | Bellew |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064088 A1 | 4/2004 | Gorman et al. |
| 2004/0064259 A1 | 4/2004 | Haaland et al. |
| 2004/0068224 A1 | 4/2004 | Alfred, Jr. et al. |
| 2004/0069044 A1 | 4/2004 | Lavi et al. |
| 2004/0085215 A1 | 5/2004 | Moberg et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell |
| 2005/0033148 A1 | 2/2005 | Haueter et al. |
| 2005/0038680 A1* | 2/2005 | McMahon ......... A61B 5/14532 |
| | | 600/300 |
| 2005/0049179 A1 | 3/2005 | Davidson et al. |
| 2005/0055242 A1 | 3/2005 | Bello et al. |
| 2005/0065464 A1 | 3/2005 | Talbot et al. |
| 2005/0065465 A1 | 3/2005 | Ebel et al. |
| 2005/0075624 A1 | 4/2005 | Miesel |
| 2005/0105095 A1 | 5/2005 | Pesach et al. |
| 2005/0134609 A1 | 6/2005 | Yu |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0182366 A1 | 8/2005 | Vogt et al. |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0262451 A1 | 11/2005 | Remignanti et al. |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0041229 A1 | 2/2006 | Garibotto et al. |
| 2006/0079765 A1 | 4/2006 | Neer et al. |
| 2006/0079809 A1 | 4/2006 | Goldberger et al. |
| 2006/0086909 A1 | 4/2006 | Schaber |
| 2006/0086994 A1 | 4/2006 | Viefers et al. |
| 2006/0092569 A1 | 5/2006 | Che et al. |
| 2006/0100494 A1 | 5/2006 | Kroll |
| 2006/0134323 A1 | 6/2006 | OBrien |
| 2006/0134491 A1 | 6/2006 | Hilchenko et al. |
| 2006/0167350 A1 | 7/2006 | Monfre et al. |
| 2006/0173406 A1 | 8/2006 | Hayes et al. |
| 2006/0178633 A1 | 8/2006 | Garibotto et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0264926 A1 | 11/2006 | Kochamba |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0027370 A1 | 2/2007 | Brauker et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0078784 A1 | 4/2007 | Donovan et al. |
| 2007/0083160 A1 | 4/2007 | Hall et al. |
| 2007/0100635 A1 | 5/2007 | Mahajan et al. |
| 2007/0106135 A1 | 5/2007 | Sloan et al. |
| 2007/0112298 A1 | 5/2007 | Mueller et al. |
| 2007/0116601 A1 | 5/2007 | Patton |
| 2007/0118405 A1 | 5/2007 | Campbell |
| 2007/0129690 A1 | 6/2007 | Rosenblatt et al. |
| 2007/0142720 A1 | 6/2007 | Ridder et al. |
| 2007/0166453 A1 | 7/2007 | Van Duren et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0179885 A1 | 8/2007 | Bird et al. |
| 2007/0191702 A1 | 8/2007 | Yodfat |
| 2007/0191716 A1 | 8/2007 | Goldberger et al. |
| 2007/0191770 A1 | 8/2007 | Moberg et al. |
| 2007/0197163 A1 | 8/2007 | Robertson |
| 2007/0225675 A1 | 9/2007 | Robinson et al. |
| 2007/0233051 A1 | 10/2007 | Hohl et al. |
| 2007/0244381 A1 | 10/2007 | Robinson et al. |
| 2007/0249007 A1 | 10/2007 | Rosero |
| 2007/0259768 A1 | 11/2007 | Kear et al. |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0004515 A1 | 1/2008 | Jennewine |
| 2008/0027371 A1 | 1/2008 | Higuchi et al. |
| 2008/0033272 A1 | 2/2008 | Gough et al. |
| 2008/0051738 A1 | 2/2008 | Griffin |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0077081 A1 | 3/2008 | Mounce et al. |
| 2008/0078400 A1 | 4/2008 | Martens et al. |
| 2008/0097289 A1 | 4/2008 | Steil et al. |
| 2008/0114304 A1 | 5/2008 | Nalesso et al. |
| 2008/0132880 A1 | 6/2008 | Buchman |
| 2008/0160492 A1 | 7/2008 | Campbell et al. |
| 2008/0161664 A1 | 7/2008 | Mastrototaro et al. |
| 2008/0172026 A1 | 7/2008 | Blomquist |
| 2008/0172028 A1 | 7/2008 | Blomquist |
| 2008/0172031 A1 | 7/2008 | Blomquist |
| 2008/0173073 A1 | 7/2008 | Downie et al. |
| 2008/0177165 A1 | 7/2008 | Blomquist et al. |
| 2008/0188796 A1 | 8/2008 | Steil et al. |
| 2008/0200838 A1 | 8/2008 | Goldberger et al. |

(56)                References Cited

U.S. PATENT DOCUMENTS

| | | |
|---|---|---|
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0255438 A1 | 10/2008 | Saidara et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0281290 A1 | 11/2008 | Yodfat et al. |
| 2008/0287906 A1 | 11/2008 | Burkholz et al. |
| 2009/0006061 A1 | 1/2009 | Thukral et al. |
| 2009/0018406 A1 | 1/2009 | Yodfat |
| 2009/0030398 A1 | 1/2009 | Yodfat |
| 2009/0036753 A1 | 2/2009 | King |
| 2009/0043240 A1 | 2/2009 | Robinson et al. |
| 2009/0048556 A1 | 2/2009 | Durand |
| 2009/0054753 A1 | 2/2009 | Robinson et al. |
| 2009/0062767 A1 | 3/2009 | Van Antwerp et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0112769 A1 | 4/2009 | Dicks et al. |
| 2009/0131861 A1 | 5/2009 | Braig et al. |
| 2009/0143661 A1* | 6/2009 | Taub ..................... G16H 40/67 |
| | | 600/365 |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0177142 A1 | 7/2009 | Blomquist et al. |
| 2009/0177147 A1 | 7/2009 | Blomquist |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0254041 A1 | 10/2009 | Krag et al. |
| 2009/0318791 A1 | 12/2009 | Kaastrup |
| 2009/0326343 A1 | 12/2009 | Gable et al. |
| 2009/0326472 A1 | 12/2009 | Carter |
| 2010/0017141 A1 | 1/2010 | Campbell et al. |
| 2010/0036326 A1 | 2/2010 | Matusch |
| 2010/0057042 A1 | 3/2010 | Hayter |
| 2010/0064243 A1 | 3/2010 | Buck et al. |
| 2010/0076275 A1 | 3/2010 | Chu et al. |
| 2010/0077198 A1 | 3/2010 | Buck et al. |
| 2010/0094251 A1 | 4/2010 | Estes |
| 2010/0114026 A1 | 5/2010 | Karratt |
| 2010/0121170 A1 | 5/2010 | Rule |
| 2010/0137784 A1 | 6/2010 | Cefai et al. |
| 2010/0145272 A1 | 6/2010 | Cefai et al. |
| 2010/0152658 A1 | 6/2010 | Hanson et al. |
| 2010/0174228 A1 | 7/2010 | Buckingham et al. |
| 2010/0185175 A1 | 7/2010 | Kamen |
| 2010/0185183 A1 | 7/2010 | Alme et al. |
| 2010/0211003 A1 | 8/2010 | Sundar et al. |
| 2010/0228110 A1 | 9/2010 | Tsoukalis |
| 2010/0241066 A1 | 9/2010 | Hansen et al. |
| 2010/0262117 A1 | 10/2010 | Magni et al. |
| 2010/0262434 A1 | 10/2010 | Shaya |
| 2010/0286997 A1 | 11/2010 | Srinivasan |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0049394 A1 | 3/2011 | de Rochemont |
| 2011/0054390 A1 | 3/2011 | Searle et al. |
| 2011/0054399 A1 | 3/2011 | Chong et al. |
| 2011/0065224 A1 | 3/2011 | Bollman et al. |
| 2011/0071765 A1 | 3/2011 | Yodfat et al. |
| 2011/0124996 A1 | 5/2011 | Reinke et al. |
| 2011/0142688 A1 | 6/2011 | Chappel et al. |
| 2011/0144586 A1 | 6/2011 | Michaud et al. |
| 2011/0152658 A1 | 6/2011 | Peyser et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0213306 A1 | 9/2011 | Hanson et al. |
| 2011/0218495 A1 | 9/2011 | Remde |
| 2011/0225024 A1 | 9/2011 | Seyer et al. |
| 2011/0230833 A1 | 9/2011 | Landman et al. |
| 2011/0246235 A1 | 10/2011 | Powell et al. |
| 2011/0251509 A1 | 10/2011 | Beyhan et al. |
| 2011/0257496 A1* | 10/2011 | Terashima ............. A61B 5/416 |
| | | 600/347 |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0029941 A1 | 2/2012 | Malave et al. |
| 2012/0030393 A1 | 2/2012 | Ganesh et al. |
| 2012/0050046 A1 | 3/2012 | Satorius et al. |
| 2012/0053556 A1 | 3/2012 | Lee |
| 2012/0054841 A1 | 3/2012 | Schultz et al. |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas |
| 2012/0124521 A1 | 5/2012 | Guo |
| 2012/0136336 A1 | 5/2012 | Mastrototaro et al. |
| 2012/0150446 A1 | 6/2012 | Chang et al. |
| 2012/0153936 A1 | 6/2012 | Romani et al. |
| 2012/0172833 A1 | 7/2012 | Zisapel |
| 2012/0182939 A1 | 7/2012 | Rajan et al. |
| 2012/0184909 A1 | 7/2012 | Gyrn |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0219935 A1* | 8/2012 | Stebbings ................ G09B 7/06 |
| | | 434/262 |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0250449 A1 | 10/2012 | Nakano |
| 2012/0265166 A1 | 10/2012 | Yodfat |
| 2012/0271655 A1 | 10/2012 | Knobel et al. |
| 2012/0277667 A1 | 11/2012 | Yodat et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0030841 A1 | 1/2013 | Bergstrom et al. |
| 2013/0036100 A1 | 2/2013 | Nagpal et al. |
| 2013/0060194 A1 | 3/2013 | Rostein |
| 2013/0080832 A1 | 3/2013 | Dean et al. |
| 2013/0138452 A1 | 5/2013 | Cork et al. |
| 2013/0158503 A1 | 6/2013 | Kanderian, Jr. et al. |
| 2013/0172695 A1 | 7/2013 | Nielsen et al. |
| 2013/0172710 A1 | 7/2013 | Mears et al. |
| 2013/0173473 A1 | 7/2013 | Birtwhistle et al. |
| 2013/0178791 A1 | 7/2013 | Javitt |
| 2013/0231642 A1 | 9/2013 | Doyle et al. |
| 2013/0245545 A1 | 9/2013 | Arnold et al. |
| 2013/0253472 A1 | 9/2013 | Cabiri |
| 2013/0261406 A1 | 10/2013 | Rebec et al. |
| 2013/0274576 A1 | 10/2013 | Amirouche et al. |
| 2013/0296792 A1 | 11/2013 | Cabiri |
| 2013/0296823 A1 | 11/2013 | Melker et al. |
| 2013/0298080 A1 | 11/2013 | Griffin et al. |
| 2013/0317753 A1 | 11/2013 | Kamen et al. |
| 2013/0332874 A1 | 12/2013 | Rosinko et al. |
| 2013/0338576 A1 | 12/2013 | OConnor et al. |
| 2013/0346858 A1 | 12/2013 | Neyrinck |
| 2014/0005633 A1 | 1/2014 | Finan |
| 2014/0018730 A1 | 1/2014 | Muller-Pathle |
| 2014/0032549 A1 | 1/2014 | McDaniel et al. |
| 2014/0066886 A1 | 3/2014 | Roy et al. |
| 2014/0066887 A1 | 3/2014 | Mastrototaro et al. |
| 2014/0074033 A1 | 3/2014 | Sonderegger et al. |

(56) References Cited

U.S. PATENT DOCUMENTS

| | | |
|---|---|---|
| 2014/0074059 A1* | 3/2014 | Howell ............ A61M 5/14244 |
| | | 604/503 |
| 2014/0088428 A1 | 3/2014 | Yang et al. |
| 2014/0108046 A1 | 4/2014 | Cabrera et al. |
| 2014/0114277 A1 | 4/2014 | Eggert et al. |
| 2014/0121635 A1 | 5/2014 | Hayter |
| 2014/0128839 A1 | 5/2014 | Dilanni et al. |
| 2014/0129951 A1 | 5/2014 | Amin et al. |
| 2014/0135880 A1 | 5/2014 | Baumgartner et al. |
| 2014/0142508 A1 | 5/2014 | Dilanni et al. |
| 2014/0146202 A1 | 5/2014 | Boss et al. |
| 2014/0163664 A1 | 6/2014 | Goldsmith |
| 2014/0171901 A1 | 6/2014 | Langsdorf et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0025503 A1 | 1/2015 | Searle et al. |
| 2015/0038898 A1 | 2/2015 | Palmer et al. |
| 2015/0041498 A1 | 2/2015 | Kakiuchi et al. |
| 2015/0057913 A1 | 2/2015 | Benhammou |
| 2015/0119666 A1 | 4/2015 | Brister et al. |
| 2015/0120317 A1 | 4/2015 | Mayou et al. |
| 2015/0134265 A1 | 5/2015 | Kohlbrecher et al. |
| 2015/0134353 A1 | 5/2015 | Ferrell et al. |
| 2015/0151050 A1 | 6/2015 | Estes |
| 2015/0165119 A1 | 6/2015 | Palerm et al. |
| 2015/0173674 A1 | 6/2015 | Hayes et al. |
| 2015/0193585 A1 | 7/2015 | Sunna |
| 2015/0202386 A1 | 7/2015 | Brady et al. |
| 2015/0205509 A1 | 7/2015 | Scriven et al. |
| 2015/0205511 A1 | 7/2015 | Vinna et al. |
| 2015/0213217 A1 | 7/2015 | Amarasingham et al. |
| 2015/0217046 A1 | 8/2015 | Heller |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0290391 A1 | 10/2015 | Schmid et al. |
| 2015/0301691 A1 | 10/2015 | Qin |
| 2015/0306314 A1 | 10/2015 | Doyle et al. |
| 2015/0331995 A1 | 11/2015 | Zhao et al. |
| 2015/0351671 A1 | 12/2015 | Vanslyke et al. |
| 2015/0352280 A1* | 12/2015 | Deratany ............ A61B 5/4839 |
| | | 604/67 |
| 2015/0356250 A1 | 12/2015 | Polimeni |
| 2015/0366945 A1 | 12/2015 | Greene et al. |
| 2016/0015891 A1 | 1/2016 | Papiorek |
| 2016/0019352 A1 | 1/2016 | Cohen et al. |
| 2016/0022905 A1 | 1/2016 | Nagar et al. |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0184517 A1 | 6/2016 | Baek et al. |
| 2016/0220181 A1 | 8/2016 | Rigooard et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0259889 A1 | 9/2016 | Murtha et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0339172 A1 | 11/2016 | Michaud et al. |
| 2016/0354543 A1 | 12/2016 | Cinar et al. |
| 2017/0021096 A1 | 1/2017 | Cole et al. |
| 2017/0049386 A1 | 2/2017 | Abraham et al. |
| 2017/0053552 A1 | 2/2017 | Zhong |
| 2017/0131887 A1 | 5/2017 | Kim et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0213002 A1 | 7/2017 | Jha |
| 2017/0216524 A1 | 8/2017 | Haider et al. |
| 2017/0239415 A1 | 8/2017 | Hwang et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0332951 A1 | 11/2017 | Ahmad |
| 2017/0348482 A1 | 12/2017 | Duke et al. |
| 2018/0014113 A1 | 1/2018 | Boesen |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277246 A1 | 9/2018 | Zhong |
| 2018/0277253 A1 | 9/2018 | Gondhalekar et al. |
| 2018/0280609 A1 | 10/2018 | Nishimura et al. |
| 2018/0289891 A1 | 10/2018 | Finan et al. |
| 2018/0296757 A1 | 10/2018 | Finan et al. |
| 2018/0307515 A1 | 10/2018 | Meller et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0095052 A1 | 3/2019 | De Wever et al. |
| 2019/0132801 A1 | 5/2019 | Kamath et al. |
| 2019/0184091 A1 | 6/2019 | Sjolund et al. |
| 2019/0240403 A1 | 8/2019 | Palerm et al. |
| 2019/0290844 A1 | 9/2019 | Monirabbasi et al. |
| 2019/0321545 A1 | 10/2019 | Saint |
| 2019/0336683 A1 | 11/2019 | O'Connor |
| 2019/0336684 A1 | 11/2019 | O'Connor et al. |
| 2019/0348157 A1 | 11/2019 | Booth et al. |
| 2019/0374714 A1 | 12/2019 | Rioux et al. |
| 2020/0001006 A1 | 1/2020 | Pizzochero et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0101286 A1 | 4/2020 | Windmiller |
| 2020/0113515 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2021/0225480 A1 | 7/2021 | Desborough |
| 2022/0023536 A1 | 1/2022 | Graham et al. |
| 2022/0273872 A1 | 9/2022 | Narayanaswami |
| 2023/0128193 A1 | 4/2023 | Williams |
| 2023/0338652 A1 | 10/2023 | Narayanaswami |
| 2023/0343430 A1 | 10/2023 | Narayanaswami |
| 2024/0099612 A1 | 3/2024 | Budiman |
| 2024/0206772 A1 | 6/2024 | Hayter |
| 2024/0306949 A1 | 9/2024 | Kumar |
| 2025/0255560 A1 | 8/2025 | Williams |

FOREIGN PATENT DOCUMENTS

| | | | |
|---|---|---|---|
| CA | 2863379 A1 | 8/2013 |
| CN | 1297140 A | 5/2001 |
| CN | 101208699 A | 6/2008 |
| CN | 201134101 Y | 10/2008 |
| DE | 4200595 A1 | 7/1993 |

(56) References Cited

FOREIGN PATENT DOCUMENTS

| | | | |
|---|---|---|---|
| DE | 19756872 | A1 | 7/1999 |
| EP | 0026056 | A1 | 4/1981 |
| EP | 0341049 | A2 | 11/1989 |
| EP | 0496305 | A2 | 7/1992 |
| EP | 0549341 | A1 | 6/1993 |
| EP | 0867196 | A2 | 9/1998 |
| EP | 0939451 | A1 | 9/1999 |
| EP | 1177802 | A1 | 2/2002 |
| EP | 1376759 | A2 | 1/2004 |
| EP | 1491144 | A1 | 12/2004 |
| EP | 0801578 | B1 | 7/2006 |
| EP | 1762263 | A1 | 3/2007 |
| EP | 1839694 | A1 | 10/2007 |
| EP | 1852703 | A1 | 11/2007 |
| EP | 2099384 | A1 | 9/2009 |
| EP | 2139382 | A1 | 1/2010 |
| EP | 2353628 | A2 | 8/2011 |
| EP | 2397181 | A1 | 12/2011 |
| EP | 2468338 | A1 | 6/2012 |
| EP | 2666520 | A1 | 11/2013 |
| EP | 2695573 | A2 | 2/2014 |
| EP | 2703024 | A1 | 3/2014 |
| EP | 1874390 | B1 | 10/2014 |
| EP | 2830499 | A1 | 2/2015 |
| EP | 2943149 | A1 | 11/2015 |
| EP | 3068290 | A1 | 9/2016 |
| EP | 3177344 | A1 | 6/2017 |
| EP | 3187201 | A1 | 7/2017 |
| EP | 3193979 | A1 | 7/2017 |
| EP | 3314548 | A1 | 5/2018 |
| EP | 1571582 | B1 | 4/2019 |
| EP | 2897071 | B1 | 5/2019 |
| EP | 3598942 | A1 | 1/2020 |
| EP | 3607985 | A1 | 2/2020 |
| ES | 2559866 | T3 | 2/2016 |
| FR | 2096275 | A5 | 2/1972 |
| GB | 1125897 | A | 9/1968 |
| GB | 1401588 | A | 7/1975 |
| GB | 2176595 | A | 12/1986 |
| GB | 2443260 | A | 4/2008 |
| GB | 2443261 | A | 4/2008 |
| GB | 2461086 | A | 12/2009 |
| GB | 2495014 | A | 3/2013 |
| GB | 2524717 | A | 10/2015 |
| GB | 2525149 | A | 10/2015 |
| JP | 51125993 | A | 11/1976 |
| JP | 02131777 | A | 5/1990 |
| JP | 2001190659 | A | 7/2001 |
| JP | 2003154190 | A | 5/2003 |
| JP | 2005326943 | A | 11/2005 |
| JP | 2007144141 | A1 | 6/2007 |
| JP | 2004283378 | A | 10/2007 |
| JP | 2007307359 | A | 11/2007 |
| JP | 2008513142 | A | 5/2008 |
| JP | 2008242502 | A | 10/2008 |
| JP | 2012210441 | A | 11/2012 |
| JP | 2017525451 | A | 9/2017 |
| JP | 2018153569 | A | 10/2018 |
| JP | 2019525276 | A | 9/2019 |
| NO | 2015081337 | A2 | 6/2015 |
| TW | 200740148 | A | 10/2007 |
| TW | M452390 | U | 5/2013 |
| WO | 200048112 | A2 | 9/1968 |
| WO | 8606796 | A1 | 11/1986 |
| WO | 9800193 | A1 | 1/1998 |
| WO | 9801071 | A1 | 1/1998 |
| WO | 9819145 | A1 | 5/1998 |
| WO | 9824495 | A1 | 6/1998 |
| WO | 9841267 | A1 | 9/1998 |
| WO | 9855073 | A1 | 12/1998 |
| WO | 9910040 | A1 | 3/1999 |
| WO | 9910049 | A1 | 3/1999 |
| WO | 9956803 | A1 | 11/1999 |
| WO | 9962576 | A1 | 12/1999 |
| WO | 0010628 | A2 | 3/2000 |
| WO | 0013580 | A1 | 3/2000 |
| WO | 0019887 | A1 | 4/2000 |
| WO | 0030705 | A1 | 6/2000 |
| WO | 200032258 | A1 | 6/2000 |
| WO | 0061215 | A1 | 10/2000 |
| WO | 0078210 | A1 | 12/2000 |
| WO | 0172354 | A2 | 10/2001 |
| WO | 2001078812 | A1 | 10/2001 |
| WO | 2002015954 | A1 | 2/2002 |
| WO | 0226282 | A2 | 4/2002 |
| WO | 2002043866 | A2 | 6/2002 |
| WO | 2002076535 | A1 | 10/2002 |
| WO | 2002082990 | A1 | 10/2002 |
| WO | 2003016882 | A1 | 2/2003 |
| WO | 2003039362 | A1 | 5/2003 |
| WO | 2003045233 | A1 | 6/2003 |
| WO | 2003097133 | A1 | 11/2003 |
| WO | 2004043250 | A1 | 5/2004 |
| WO | 2005110601 | A1 | 5/2004 |
| WO | 2004092715 | A1 | 10/2004 |
| WO | 2005031631 | A2 | 4/2005 |
| WO | 2005051170 | A2 | 6/2005 |
| WO | 2005082436 | A1 | 9/2005 |
| WO | 2005113036 | A1 | 12/2005 |
| WO | 2006053007 | A2 | 5/2006 |
| WO | 2006060668 | A2 | 6/2006 |
| WO | 2007064835 | A2 | 6/2007 |
| WO | 2007066152 | A2 | 6/2007 |
| WO | 2007078937 | A1 | 7/2007 |
| WO | 2007112034 | A2 | 10/2007 |
| WO | 2008024810 | A2 | 2/2008 |
| WO | 2008024814 | A2 | 2/2008 |
| WO | 2008029403 | A1 | 3/2008 |
| WO | 2008133702 | A1 | 11/2008 |
| WO | 2009023634 | A2 | 2/2009 |
| WO | 2009032399 | A1 | 3/2009 |
| WO | 2009039203 | A2 | 3/2009 |
| WO | 2009045462 | A1 | 4/2009 |
| WO | 2009049252 | A1 | 4/2009 |
| WO | 2009066287 | A3 | 5/2009 |
| WO | 2009066288 | A1 | 5/2009 |
| WO | 2009098648 | A2 | 8/2009 |
| WO | 2009134380 | A2 | 11/2009 |
| WO | 2010022069 | A2 | 2/2010 |
| WO | 2010025433 | A1 | 3/2010 |
| WO | 2010053702 | A1 | 5/2010 |
| WO | 2010077279 | A1 | 7/2010 |
| WO | 2010078434 | A2 | 7/2010 |
| WO | 2010132077 | A1 | 11/2010 |
| WO | 2010138848 | A1 | 12/2010 |
| WO | 2010139793 | A1 | 12/2010 |
| WO | 2010146579 | A1 | 12/2010 |
| WO | 2010147659 | A2 | 12/2010 |
| WO | 2011012465 | A1 | 2/2011 |
| WO | 2011031458 | A1 | 3/2011 |
| WO | 2011075042 | A1 | 6/2011 |
| WO | 2011095483 | A1 | 8/2011 |
| WO | 2011133823 | A1 | 10/2011 |
| WO | 2012045667 | A2 | 4/2012 |
| WO | 2012073032 | A1 | 6/2012 |
| WO | 2012108959 | A1 | 8/2012 |
| WO | 2012134588 | A1 | 10/2012 |
| WO | 2012177353 | A1 | 12/2012 |
| WO | 2012178134 | A2 | 12/2012 |
| WO | 2013050535 | A2 | 4/2013 |
| WO | 2013078200 | A1 | 5/2013 |
| WO | 2013134486 | A2 | 9/2013 |
| WO | 2013149186 | A1 | 10/2013 |
| WO | 20130149186 | A1 | 10/2013 |
| WO | 2013177565 | A1 | 11/2013 |
| WO | 2013182321 | A1 | 12/2013 |
| WO | 2014029416 | A1 | 2/2014 |
| WO | 2014109898 | A1 | 7/2014 |
| WO | 2014110538 | A1 | 7/2014 |
| WO | 2014136105 | A1 | 9/2014 |
| WO | 2014149357 | A1 | 9/2014 |
| WO | 2014179774 | A1 | 11/2014 |
| WO | 2014194183 | A2 | 12/2014 |
| WO | 2015056259 | A1 | 4/2015 |

(56) References Cited

FOREIGN PATENT DOCUMENTS

| WO | 2015061493 A1 | 4/2015 |
| WO | 2015073211 A1 | 5/2015 |
| WO | 2015117082 A1 | 8/2015 |
| WO | 2015117854 A1 | 8/2015 |
| WO | 2015167201 A1 | 11/2015 |
| WO | 2015177082 A1 | 11/2015 |
| WO | 2015187366 A1 | 12/2015 |
| WO | 2015187793 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2016181384 A2 | 11/2016 |
| WO | 2017004278 A1 | 1/2017 |
| WO | 2017089289 A1 | 6/2017 |
| WO | 2017091624 A1 | 6/2017 |
| WO | 2017105600 A1 | 6/2017 |
| WO | 2017184988 A1 | 10/2017 |
| WO | 2017187177 A1 | 11/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019043702 A1 | 3/2019 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2020124058 A1 | 6/2020 |
| WO | 2021011738 A1 | 1/2021 |

OTHER PUBLICATIONS

Lee, et al. "The Clinical Case for the Integration of a Ketone Sensor as Part of a Closed Loop Insulin Pump System," Journal of Diabetes Science and Technology 2019, vol. 13(5) 967-973 (Year: 2019).*

Laffel, et al., "ISPAD Clinical Practice Consensus Guidelines 2018: Sick day management in children and adolescents with diabetes," Received: Jul. 19, 2018, DOI: 10.1111/pedi.12741 (Year: 2018).*

Mencher, et al., "Sick Day Management," First Online: Feb. 13, 2021, pp. 125-133. (Year: 2021).*

Fuchs, et al. "Benefits and Challenges of Current Closed-Loop Technologies in Children and Young People With Type1 Diabetes," Mini Review published: Apr. 30, 2021, doi: 10.3389/fped.2021.679484 (Year: 2021).*

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., "Control-Relevant Models for Glucose Control using a Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, mailed May 16, 2017, 12 pages.

International Search Report and Written Opinion for the International Patent Application No. PCT/US2018/018901, mailed on Aug. 6, 2018, 12 pages.

International Search Report and Written Opinion for International Patent Application No. PCT/US2018/052467, mailed Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.

"Read NFC Tags with an iPHone App on iOS 11", GoToTags, Sep. 11, 2017, web <https://gototags.com/blog/read-nfc-tags-with-an-iphone-app-on-ios-11/>. (Year:2017).

International Search Report and Written Opinion for International Patent Application No. PCT/US2016/063350, mailed on Mar. 27, 2017, 9 pages.

Extended Search Report mailed Aug. 13, 2018, issued in European Patent Application No. 16753053.4, 9 pages.

International Search Report and Written Opinion for International Patent Application No. PCT/US16/18452, mailed on Apr. 29, 2015, 9 pages.

International Preliminary Report on Patentability mailed Aug. 31, 2017, issued in PCT Patent Application No. PCT/US2016/018452, 7 pages.

International Search Report and Written Opinion for International Patent Application No. PCT/US2019/055862, mailed on Mar. 11, 2020.

International Search Report and Written Opinion for Application No. PCT/US2019/030562, Sep. 25, 2019, 19 pages.

Lee, Melissa H. et al: "The Clinical Case for the Integration of a Ketone Sensor as Part of a Closed Loop Insulin Pup System", Journal of Diabetes Science and Technology Diabetes Technology Society, vol. 13(5), Dec. 31, 2019 (Dec. 31, 2019), pp. 967-973.

Rometo, David et al: "Perioperative Glycemic Management of Patients Undergoing Bariatric Surgery", Current Diabetes Reports, Current Science, Philadelphia, VA, US, vol. 16, No. 4, Feb. 15, 2016 (Feb. 15, 2016), pp. 1-8.

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

European Patent Office, "Notification of Transmittal of the ISR and the Written Opinion of the International Searching Authority, or the Declaration," in PCT Application No. PCT/GB2015/050248, Jun. 23, 2015, 12 pages.

International Search Report and Written Opinion for the International Patent Application No. PCT/US2021/012246, mailed Apr. 13, 2021, 15 pages.

International Search Report and Written Opinion for the International Patent Application No. PCT/US2021/013639, mailed Apr. 28, 2021, 14 pages.

International Search Report and Written Opinion for the International Patent Application No. PCT/US2020/063326, mailed May 3, 2021, 17 pages.

European Search Report for the European Patent Application No. 21168591, mailed Oct. 13, 2021, 4 pages.

International Search Report and Written Opinion for the International Patent Application No. PCT/US2021/041954, mailed Oct. 25, 2021, 13 pages.

International Search Report and Written Opinion for the International Patent Application No. PCT/US2021/022694, mailed Jun. 25, 2021, 13 pages.

(56) References Cited

OTHER PUBLICATIONS

International Search Report and Written Opinion for the International Patent Application No. PCT/US2021/017664, mailed May 26, 2021, 16 pages.

International Search Report and Written Opinion for the International Patent Application No. PCT/US2022/012896, mailed Apr. 22, 2022, 15 pages.

International Search Report and Written Opinion for the International Patent Application No. PCT/US2022/013470, mailed May 6, 2022, 14 pages.

International Search Report and Written Opinion for the International Patent Application No. PCT/US2022/013473, mailed May 6, 2022, 13 pages.

International Search Report and Written Opinion for the International Patent Application No. PCT/US2022/019079, mailed Jun. 2, 2022, 14 pages.

International Search Report and Written Opinion for the International Patent Application No. PCT/US2022/018453, mailed Jun. 2, 2022, 13 pages.

International Search Report and Written Opinion for the International Patent Application No. PCT/US22/018700, mailed Jun. 7, 2022, 13 pages.

International Search Report and Written Opinion for the International Patent Application No. PCT/US22/019080, mailed Jun. 7, 2022, 14 pages.

International Search Report and Written Opinion for the International Patent Application No. PCT/US22/019664, mailed Jun. 7, 2022, 14 pages.

International Search Report and Written Opinion for International Patent Application No. PCT/US2021/051027, mailed on Jan. 7, 2022, 16 pages.

International Search Report and Written Opinion for International Patent Application No. PCT/US2021/052372, mailed Jan. 26, 2022, 15 pages.

International Search Report and Written Opinion for the International Patent Application No. PCT/US2021/046607, mailed Jan. 31, 2022, 20 pages.

International Search Report and Written Opinion for the International Patent Application No. PCT/US2021/055745, mailed Feb. 14, 2022, 13 pages.

International Search Report and Written Opinion for the International Patent Application No. PCT/US21/060618, mailed Mar. 21, 2022, 15 pages.

Herrero Pau et al: "Enhancing automatic closed-loop glucose control in type 1 diabetes with an adaptive meal polus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].

International Search Report and Written Opinion for the International Patent Application No. PCT/US2021/052855, mailed Dec. 22, 2021, 11 pages.

International Search Report and Written Opinion for the International Patent Application No. PCT/US2021/047771, mailed Dec. 22, 2021, 11 pages.

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

International Search Report and Written Opinion for the International Patent Application No. PCT/US2023/019254, mailed Jul. 25, 2023, 14 pages.

International Search Report and Written Opinion for the International Patent Application No. PCT/US2023/019256, mailed Jul. 10, 2023, 12 pages.

Maahs David M. et al: "A Randomized Trial of a Home System to Reduce Nocturnal Hypoglycemia in Type 1 Diabetes", Diabetes Care, vol. 37, No. 7, Jun. 12, 2014 (Jun. 12, 2014), pp. 1885-1891, Retrieved from the Internet: URL:https://diabetesjournals.org/care/article-pdf/37/7/1885/486685/1885.pdf>.

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, mailed Jun. 2, 2021, 15 pages.

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.

Davidson, Paul C., et al., A computer-directed intravenous insulin system shown to be safe, simple, and effective in 120,618 h of operation, Diabetes Care, vol. 28, No. 10, Oct. 2005, pp. 2418-2423.

(56) References Cited

OTHER PUBLICATIONS

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A "Microbial Contamination of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al, "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010o International Search Report and Written Opinion in PCT/US2008/079641 dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et al., "Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor, Glucon; retrieved on Dec. 29, 2010 from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, imitations, and appropriate usage," AJP-Endocrinol Metab, vol. 294, E15-E26, first published Oct. 23, 2007.

International Preliminary Report on Patentability for the International Patent Application No. PCT/US2019/053603, mailed Apr. 8, 2021, 9 pages.

International Search Report and Written Opinion for the International Patent Application No. PCT/US2019/053603, mailed Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,vol. Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

International Search Report and Written Opinion for the International Patent Application No. PCT/US2021/047690, mailed Jan. 14, 2022, 13 pages.

International Search Report and Written Opinion for the International Patent Application No. PCT/US2022/055745, mailed Feb. 14, 2022, 13 pages.

International Search Report and Written Opinion for the International Patent Application No. PCT/US2021/053162, mailed Mar. 28, 2022, 18 pages.

International Search Report and Written Opinion for the International Patent Application No. PCT/US2021/064041, mailed Apr. 29, 2022, 11 pages.

International Search Report and Written Opinion for the International Patent Application No. PCT/US20221015809, mailed Jun, 20, 2022, 15 pages International Search Report and Written Opinion for International Patent Application No. PCT/US2022/029012, mailed Aug. 19, 2022, 12 pages.

(56) References Cited

OTHER PUBLICATIONS

European Search Report for the European Patent Application No. EP03743667, dated Jul. 22, 2008.
International Search Report and Written Opinion mailed Sep. 9, 2016, issued in PCT Patent Application No. PCT/US2016/037189, 12 pages.
Preliminary Report on Patentability mailed Dec. 21, 2017, issued in PCT Patent Application No. PCT/US2016/037189.
J.K. Intellectual Property Office, GB Application No. GB 1401587. 9, "Search Report under Section 17(5)" Aug. 11, 2015, 1 page.
International Search Report and Written Opinion for PCT Application No. PCT/GB2015/050247, May 8, 2015, 14 pages.
Extended Search Report mailed Nov. 24, 2017, issued in European Patent Application No. 15779465.2, 10 pages.
International Search Report and Written Opinion for PCT Application No. PCT/US15/26875, mailed Jan. 18, 2016, 10 pages.
J.K. Intellectual Property Office, GB Application No. GB 1401588. 7, "Search Report under Section 17(5)" Aug. 17, 2015, 1 page.
J.K. Intellectual Property Office, GB Application No. GB 1401589. 5, "Search Report under Section 17" Jul. 27, 2015, 1 page.
International Search Report and Written Opinion for PCT Application No. PCT/GB2015/050250, May 7, 2015, 9 pages.
3GPP TS 23.003 V10.0.0.0 Numbering, addressing and identification. Dec. 2010.
International Search Report and Written Opinion for PCT Application No. PCT/GB2015/050251, Jun. 12, 2015, 9 pages.
European Search Report for the European Patent Application No. EP19194241, dated Oct. 22, 2019, 6 pages.
International Preliminary Report on Patentability for PCT/US2017/061095, issued on May 14, 2019, 6 pages.
International Search Report and Written Opinion for PCT/US18/52468, mailed on Feb. 26, 2019, 16 pages.
International Search Report and Written Opinion for PCT/US2017/061095, mailed on Feb. 20, 2018, 8 pages.
Andrenko et al., "EM Analysis of PBG Substrate Microstrip Circuits for Integrated Transmitter Front End" MMET Proceedings, 295-297 (2000).
Bardi et al., "Plane Wave Scattering From Frequency-Selective Surfaces by the Finite-Element Method" IEEE Transactions on Magnetics 38(2):641-644 (2002).
Chappell et al., "Composite Metamaterial Systems for Two-Dimensional Periodic Structures" IEEE, 3840387 (2002).
Cheng et al., "Preparation and Characterization of (Ba, Sr) TiO3 thin films using interdigitial electrodes" Microelectronic Engineering, 66:872-879 (2003).
Clavijo et al., "Design Methodology for Sievenpiper High-Impedance Surfaces: An Artificial Magnetic Conductor for Positive Gain Electrically Small Antennas" IEEE Transactions on Antennas and Propagation, 51(10):2678-2690 (2003).
Diaz et al., "Magnetic Loading of Artificial Magnetic Conductors for Bandwidth Enhancement" IEEE, 431-434 (2003).
Hansen "Effect of a High-Impedance Screen on a Dipole Antenna" IEEE Antennas and Wireless Propagation Letter, 1:46-49 (2002).
Joshi et al., "Processing and Characterization of Pure and Doped Ba0.6Sr0.4TiO3 thin films for tunable microsave applications" Mat. Res. Soc. Symp. Proc., 656E:DD4.9.1-DD4.9.6 (2001).
Kern et al., "Active Negative Impedance Loaded EBG Structures for the Realization of Ultra-Wideband Artificial Magnetic Conductors" IEEE, 427-430 (2003).
Kern et al., "The Synthesis of Metamaterial Ferrities for RF Applications Using Electromagnetic Bandgap Structures" IEEE, 497-500 (2003).
Kern et al., "Ultra-thin Electromagnetic Bandgap Absorbers Synthesized via Genetic Algorithms" IEEE, 1119-1122 (2003).
Kuhn et al., "Characterization of novel mono- and bifacially active semi-transparent crystalline silicon solar cells" IEEE Transactions on Electron Devices, 46(10): 2013-2017 (1999).
Kretly et al., "The Influence of the Height Variation on the Frequency Bandgap in an AMC, Artificial magnetic Conductor for Wireless Applications: an EM Experimental Design Approach" Proceedings SBMO/IEEE MTT-S IMOC, 219-223 (2003).
Lee et al., "Investigation of Electromagnetic Bandgap (EBG) Structures for Antenna Pattern Control" IEEE, 1115-1118 (2003).
McKinzie III et al., "Mitigation of Multipath Through the Use of an Artificial Magnetic Conductor for Precision CPS Surveying Antennas" IEEE, 640-643; Date of Conference: Jun. 16-21, 2002.
Monorciho et al., "Synthesis of Artificial Magnetic Conductors by Using Multilatered Frequency Selective Surfaces" IEEE Antennas and Wireless Propagation Letters, 1:196-1999 (2002).
Mosallaei et al. "Periodic Bandgap and Effective Dielectric Materials in Electromagnetics: Characterization and Applications in Nanocavities and Waveguides" IEEE Transcations on Antennas and Propagation, 51(3):549-563 (2003).
Pontes et al., "Study of the dielectric and ferroelectric properties of chemically processed BaxSr1-xTiO3 thin films" Thin Solid Films, 386(2)91-98 (2001).
Rogers et al., "AMCs Comprised of Interdigital Capacitor FSS Layers Enable Lower Cost Applications" IEEE, 411-414 (2003).
Sievenpiper et al., "Two-Dimensional Beam Steering Using an Electrically Tunable Impedance Surface" IEEE Transactions on Antennas and Propagation, 51(10):2713-2722(2003).
Sun et al., "Efficiency of Various Photonic Bandgap (PBG) Structures" 3rd Int'l. Conf. on Microwave and Millimeter Wave Technology Proceedings, 1055-1058 (2002).
Tsunemine et al., "Pt/BaxSr(1-x)TiO3/Pt Capacitor Technology for 0.15 micron Embedded Dynamic Random Access Memory" Jap. J. Appl. Phys., 43(5A):2457-2461 (2004).
Vest "Metallo-organic decomposition (MOD) processing of ferroelectric and electro-optic films: A review" Ferroelectrics, 102(1):53-68 (1990).
Viviani et al., "Positive Temperature Coefficient of Electrical Resistivity below 150k of Barium Strontium Titanate" J. Amer. Ceram. Soc. 87(4): 756-758 (2004).
Weily et al., "Antennas Based on 2-D and 3-D Electromagnetic Bandgap Materials" IEEE, 847-850 (2003).
Yang et al., "Surface Waves of Printed Antennas on Planar Artificial Periodic Dielectric Structures" IEEE Transactions on Antennas and Propagation 49(3): 444-450 (2001).
Zhang et al., "Planar Artificial magnetic Conductors and Patch Antennas" IEEE Transactions on Antennas and Propagation, 51(10):2704-2712 (2003).
Ziroff et al., "A Novel Approach for LTCC Packaging Using a PBG Structure for Shielding and Package Mode Suppression" 33rd European Microwave Conference-Munich 419-422 (2003).
International Search Report and Written Opinion for Application No. PCT/US17/61336, mailed on Jan. 25, 2018, 9 pages.
"Graph Chart." iconfinder.com. Aug. 15, 2016. Accessed Apr. 21, 2020. Available online at URL: https://www.confinder.com/iconsets/graph-chart-2>.
"Circular Progress Indicator Component for React." reactscript. com. Dec. 2, 2016. Accessed Sep. 9, 2020. Available online at URL: <http://reactscripts.com/circular-progress-indicator-component-react/>.
Kruska, Michal. "Circle progress bar." dribbble.com. Oct. 18, 2012. Accessed Apr. 21, 2020. Available online at URL: <https://dribbble.com/shots/775718-Circle-progress-bar>.
"C# custom control <circle progress bar) Xamarian Forms." stackoverflow.com. May 22, 2016. Accessed Apr. 21, 2020. Available online at URL: <https://stackoverflow.com/questions/37379868/c-sharp-custom-control-circle-progress-bar-kamarin-forms>.
International Search Report and Written Opinion for Application No. PCT/US2021/047685 mailed on Dec. 6, 2021, 15 pages.
"Circular Loader." dribbble.com. Nov. 19, 2015. Accessed Jul. 24, 2019. Available online at URL: https://dribbble.com/shots/2362441-Circular-Loader (Year: 2015).
"Creating NSSlider with 2 knobs (range slider)." stackoverflow. com. May 6, 2015. Accessed Oct. 25, 2018. Available online at URL: <https://stackoverflow.com/questions/30082809/creating-nsslider-with-2- -knobs-range-slider> (Year: 2015).

(56)         References Cited

OTHER PUBLICATIONS

"How to do a Round Slider." freecodecamp.org. Comment from Aug. 2018. Accessed Jul. 24, 2019. Available online at URL: https://www.freecodecamp.org/forum/t/how-to-do-a-round-slider/ 220375 (Year: 2018).

"Tick and cross circle shape icon . . . " depositphotos.com. Aug. 27, 2016. Accessed Feb. 1, 2019. Available online at URL:<https:// depositphotos.com/121291612/stock-illustration-tick-and-cross-circle-shape.html> (Year: 2016).

"Vector-Vector Illustration of Preloader / Buffer Shapes, or Dials with Knobs." 123rf.com. Date not available. Accessed Oct. 25, 2018. Available online at URL: <https://www.123rf.com/photo_ 37292689_stock-vector-vector-illustration- -of-preloader-buffer-shapes-or-dials-with-knobs.html> (Year: N/A).

Gad, Tess. "Framer Cheat Sheet: Slider & Range Sliders." blog. framer.com. Jun. 12, 2017. Accessed Oct. 25, 2018. Available online at URL: <https://blog.framer.com/framer-cheat-sheets-slider-range-sliders-3dd2e5a4621d> (Year: 2017).

Obaizamomwan, Osas. "How to use the new features in iOS 9 Notes App." iphonehacks.com. Sep. 12, 2015. Accessed Apr. 24, 2018. Available online at URL: https://www.iphonehacks.com/2015/09/ how-to-use-the-new-features-in-ios-9-notes-app.html.

International Search Report and Written Opinion for the International Patent Application No. PCT/US21/064056, mailed Apr. 4, 2022, 12 pages.

International Search Report and Written Opinion for the International Patent Application No. PCT/US21/064170, mailed Apr. 20, 2022, 12 pages.

Anonymous: "AndroidAPS ComponentOverview", AndroidAPS documentation, Nov. 12, 2020 (Nov. 12, 2020), pp. 1-7, Retrieved from the Internet: URL:https://github.com/openaps/AndroidAPSdocs/ blob/199ef86a900adf4b3d9c32f605eb11047bd3d62f/docs/EN/Module/ module.rst [retrieved on Apr. 11, 2022] the whole document.

Team Section—Qonto, by Christophe Kerebel, dated Dec. 12, 2018, dribbble.com [online]. Retrieved Jul. 1, 2022 from Internet <URL: https://dribbble.com/shots/5676730-Team-Section-Qonto> (Year: 2018).

* cited by examiner

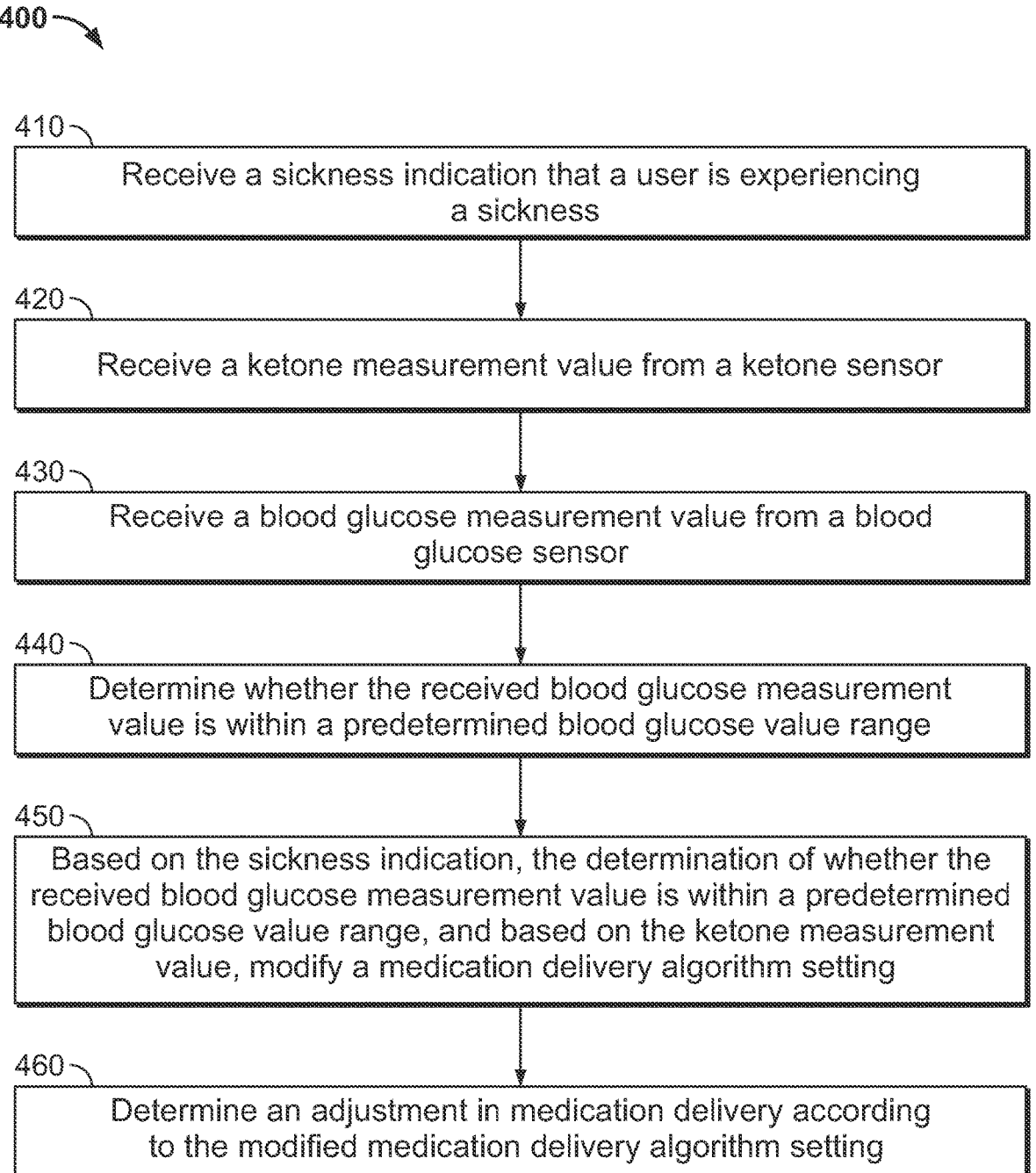

400

410
Receive a sickness indication that a user is experiencing
a sickness

420
Receive a ketone measurement value from a ketone sensor

430
Receive a blood glucose measurement value from a blood
glucose sensor

440
Determine whether the received blood glucose measurement
value is within a predetermined blood glucose value range 450
Based on the sickness indication, the determination of whether the
received blood glucose measurement value is within a predetermined
blood glucose value range, and based on the ketone measurement
value, modify a medication delivery algorithm setting 460
Determine an adjustment in medication delivery according
to the modified medication delivery algorithm setting

FIG. 4

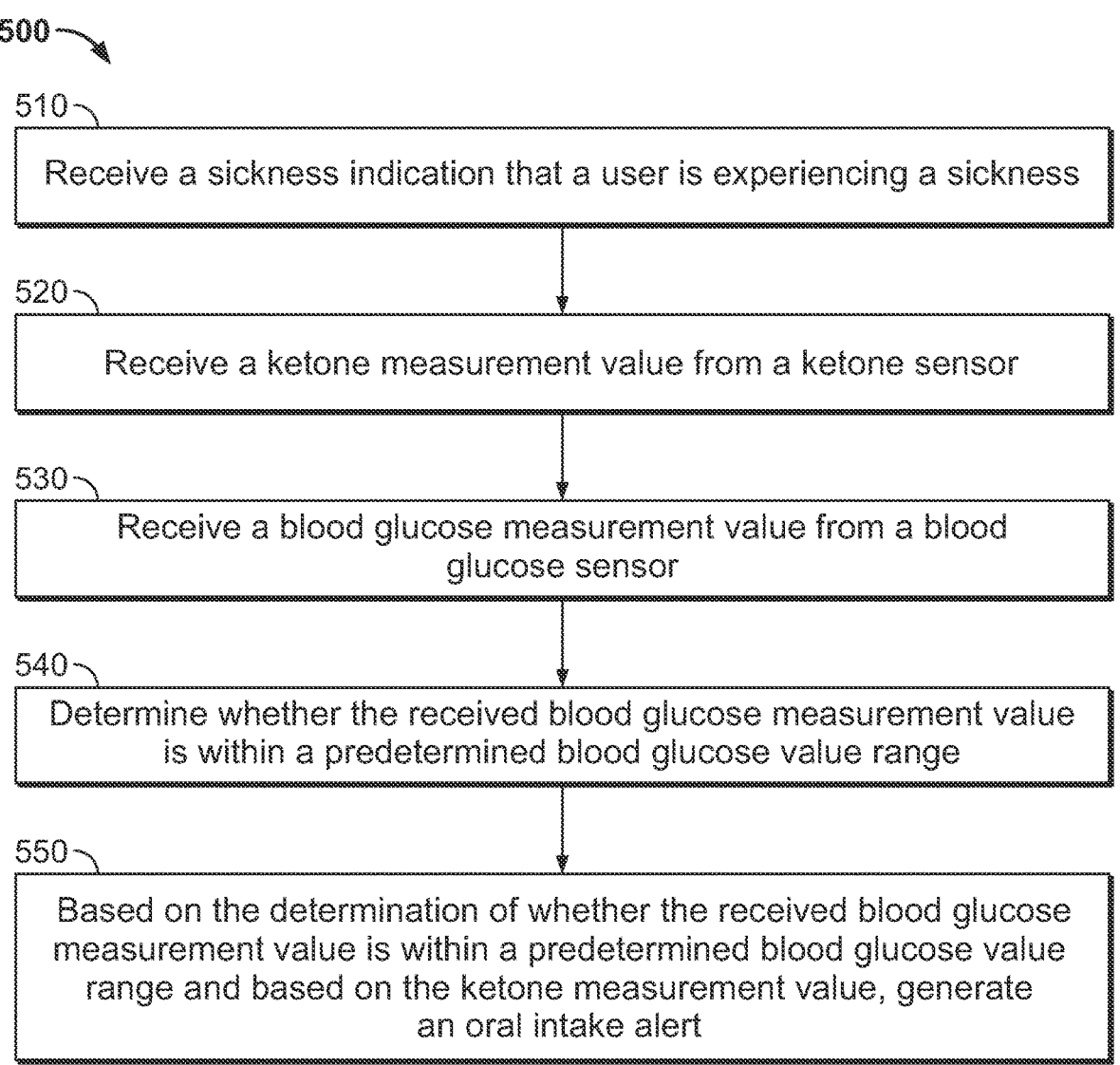

500

510
Receive a sickness indication that a user is experiencing a sickness

520
Receive a ketone measurement value from a ketone sensor

530
Receive a blood glucose measurement value from a blood glucose sensor

540
Determine whether the received blood glucose measurement value is within a predetermined blood glucose value range 550
Based on the determination of whether the received blood glucose measurement value is within a predetermined blood glucose value range and based on the ketone measurement value, generate an oral intake alert

FIG. 5

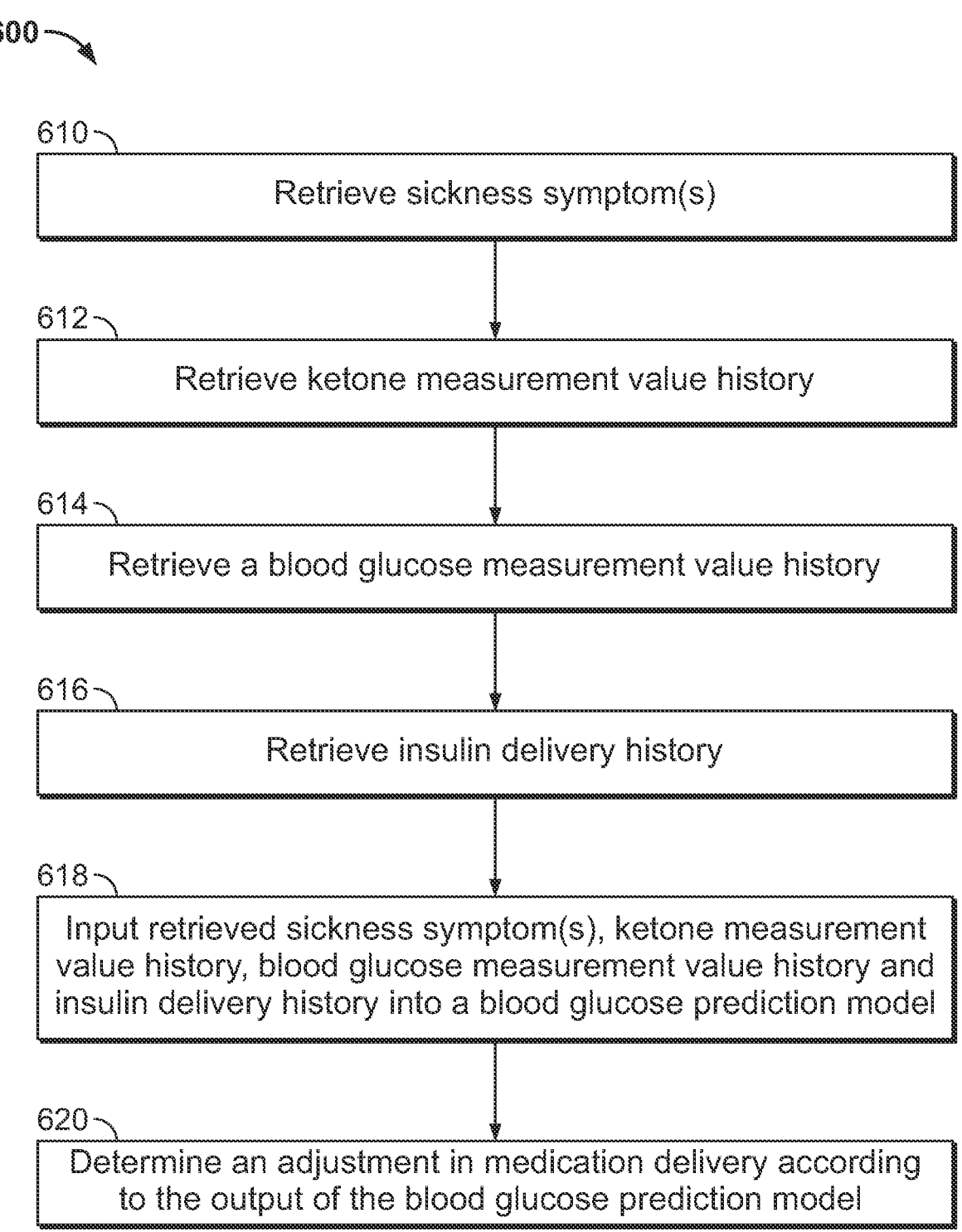

600

610  Retrieve sickness symptom(s)

612  Retrieve ketone measurement value history

614  Retrieve a blood glucose measurement value history

616  Retrieve insulin delivery history

618  Input retrieved sickness symptom(s), ketone measurement value history, blood glucose measurement value history and insulin delivery history into a blood glucose prediction model 620  Determine an adjustment in medication delivery according to the output of the blood glucose prediction model

FIG. 6

INSULIN ADAPTATION AND SAFETY MONITORING FOR SICK DAY MANAGEMENT

RELATED APPLICATIONS

This application claims the benefit of U.S. Provisional Patent Application No. 63/333,149, filed Apr. 21, 2022, the entire contents of which are incorporated herein by reference in their entirety.

BACKGROUND

Assessment of the performance of a medication delivery algorithm (MDA), such as automated insulin delivery (AID) algorithms, are often executed in a stepwise process, where a significant amount of insulin delivery data and glucose measurement data is processed. Changes in the MDA algorithm that can result in improved glucose control outcomes are applied. However, the processing of significant amounts of data may result in a significant delay in the time that it takes for each MDA algorithm to improve its behaviors.

Insulin needs and glucose levels behave differently on days when a person with diabetes (PWD) is sick. Risks of hypoglycemia, hyperglycemia as well as diabetic ketoacidosis (DKA) increase on sick days. In the context of adaptive MDA systems, this can pose challenges for optimal insulin delivery. Further, the insulin changes that happen on days during which a PWD is sick may contribute to alterations in insulin delivery after the sick day, depending on the time scale used in adapting insulin delivery. Using a "sickness" mode can keep these insulin changes separate from non-sick days so as to not skew any of a user's non-sick day data.

It would be beneficial if there was a process, devices, and techniques by which the behavior of an MDA algorithm could be modified to account for sickness (also referred to herein as illness).

BRIEF SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In one embodiment, a controller of a drug delivery system that may include a processor, a user interface, a memory, and communication circuitry is disclosed. The processor may be operable to execute programming instructions. The user interface may include a display and user input circuitry. The memory may be operable to store the programming instructions, and the communication circuitry coupled to the processor and be operable to receive and transmit wireless communication signals. The processor, when executing the programming instructions, is operable to receive an indication that a user is experiencing a sickness. A prompt may be generated that includes a list of symptoms of the sickness in which each symptom in the list of symptoms is selectable. Based on the symptoms selected in the list of symptoms, the processor may adjust one or more settings of a medication delivery algorithm; and cause delivery of a liquid drug based on the adjusted one or more settings.

Disclosed is a drug delivery system, which may include a processor, a user interface, a memory, and communication circuitry. The processor may be operable to execute programming instructions. The user interface may include a display and user input circuitry. The memory may be operable to store the programming instructions, and the communication circuitry may be coupled to the processor and may be operable to receive and transmit wireless communication signals. The processor, when executing the programming instructions, is operable to receive, via the user interface, a sickness indication that a user is experiencing a sickness or is no longer experiencing a sickness. The processor may also receive, via the communication circuitry, a ketone measurement value from a ketone sensor and/or a glucose measurement value from a glucose monitor. The processor determines whether the received glucose measurement value and/or ketone measurement value is within a predetermined glucose value and/or ketone value range. Based on the received sickness indication, the determination of whether the received glucose measurement value is within a predetermined glucose value range, and based on the ketone measurement value, the processor may modify a medication delivery algorithm setting. The processor also determines an adjustment in medication delivery according to the modified medication delivery algorithm setting.

Disclosed is a controller of a drug delivery system that may include a processor, a user interface, a memory, and communication circuitry. The processor may be operable to execute programming instructions. The user interface may include a display and user input circuitry. The memory may be operable to store the programming instructions, and the communication circuitry is coupled to the processor and is operable to receive and transmit wireless communication signals. The processor, when executing the programming instructions, is operable to receive, via the user interface, a sickness indication that a user is experiencing a sickness or is no longer experiencing a sickness. The processor may receive, via the communication circuitry, a ketone measurement value from a ketone sensor and/or a glucose measurement value from a glucose monitor. The processor may generate an alert for the user to ingest fluids, carbohydrates, or both based on the received sickness indication, a determination of whether the received glucose measurement value is within a predetermined glucose value range, and the ketone measurement value.

BRIEF DESCRIPTION OF THE DRAWINGS

FIG. 4 presents a flowchart of an exemplary process utilizing on ketone measurement values to modify medication delivery algorithm settings.

FIG. 5 presents a flowchart of an exemplary process that improves a blood glucose prediction model.

FIG. 6 illustrates an exemplary process for utilizing data learning to make modifications to a blood glucose prediction model.

DETAILED DESCRIPTION

Figure 1:
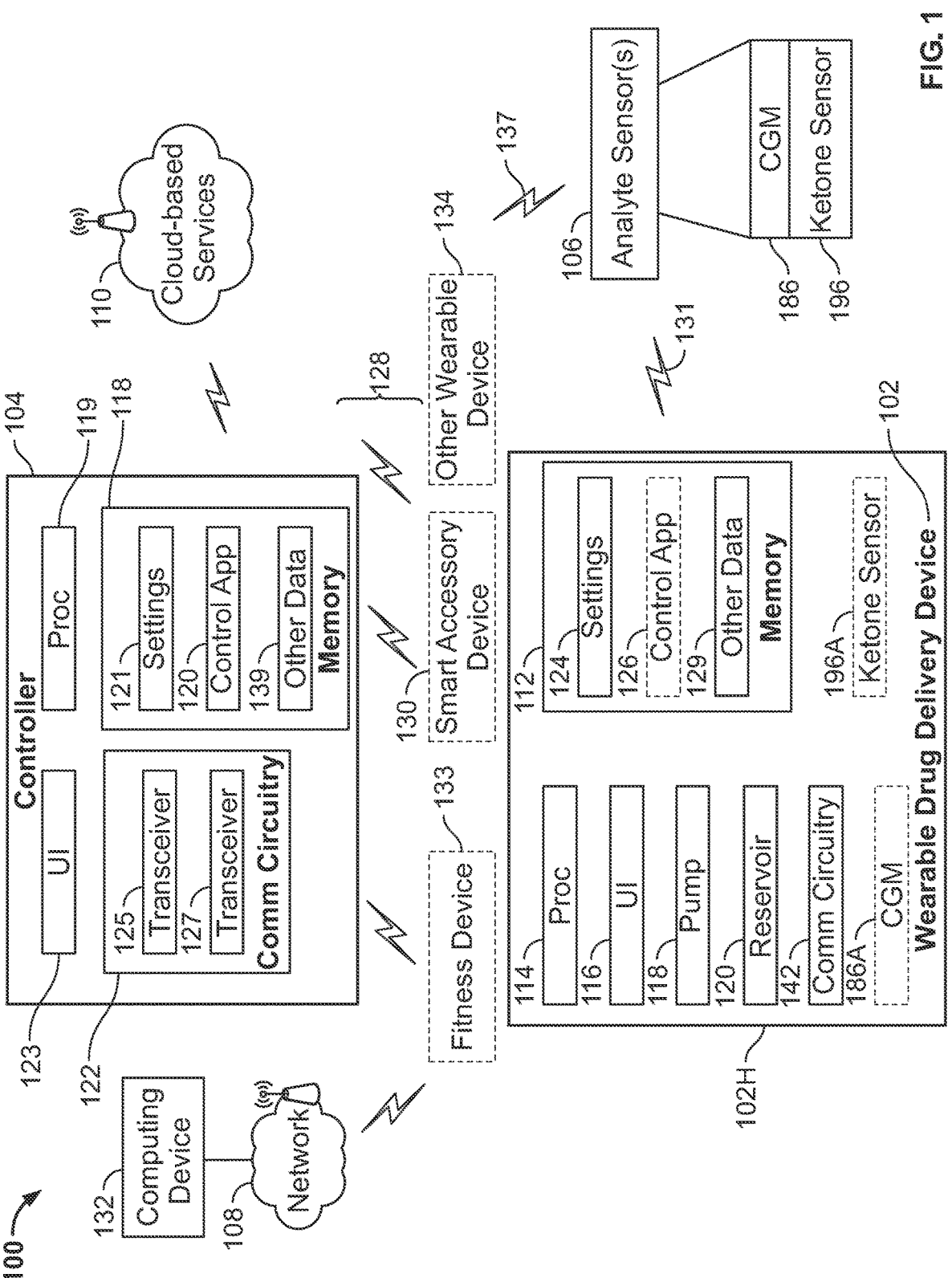
FIG. 1 illustrates an exemplary a system that is suitable to implement the subject matter described herein.

A type of medication delivery algorithm (MDA) may include an "artificial pancreas" algorithm-based system, or more generally, an artificial pancreas (AP) application. For ease of discussion, the computer programs and computer applications that implement the medication delivery algorithms or applications may be referred to herein as an "AP application," an "AID algorithm," or an "MDA." An AP application may be configured to provide automatic delivery of insulin based on an analyte sensor input, such as signals received from one or more analyte sensors, such as a continuous glucose monitor, a ketone monitor, and the like. The signals from the respective analyte sensor may contain glucose measurement values, ketone measurement values, respective timestamps of when the respective measurement values were obtained, or the like.

Additionally, or alternatively, a drug delivery system that utilizes the MDA algorithm may also use a subcutaneous embedded/auxiliary ketone sensor to continuously, or substantially continuously, monitor ketone levels. In other embodiments, blood ketones or urine ketone levels may be used.

The following describes the benefit of an MDA algorithm that is provided with a "sickness mode." The sickness mode may include a sick day (or another period of time), ketone monitoring, insulin delivery adaptation, and/or safety alerts or announcements. In an example of a safety announcement, a user interface on a smartphone, smartwatch, or a portable diabetes manager (PDM) is described with examples that allow a user to indicate initiation (or deactivation) of a sickness mode, or that 'today is a sick day,' with optional sub menus to describe the specific sickness attributes.

The basal and bolus drug deliveries (e.g., insulin) may also be analyzed by the AID system and may be adapted based on initiation or deactivation of the sickness mode and/or indicated sickness symptoms. The analysis and insulin adaptation by the process may be used to provide both symptomatic hyperglycemia and hypoglycemia avoidance. In addition, the processor may be able to keep these insulin changes separate from non-sick days (or when the sickness mode is not activated).

Additionally, or alternatively, safety alerts for impending diabetes-related ketoacidosis (DKA), hypoglycemia, hyperglycemia, and/or need to get medical attention may be provided.

In addition, or alternatively, while the disclosed examples may have been described with reference to a closed loop algorithmic implementation, variations of the disclosed examples may be implemented to enable open loop or hybrid closed-loop use. The open loop implementations allow for use of different modalities of delivery of insulin such as smart pen, syringe, or the like. For example, the disclosed AP application and algorithms may be operable to perform various functions related to open loop operations, such as the generation of prompts requesting the input of information such as diabetes type, weight, and/or age. Similarly, a dosage amount of insulin may be received by the AP application or algorithm from a user via a user interface (e.g., for a manual meal bolus). Other open-loop actions may also be implemented by adjusting user settings or the like in an AP application or algorithm.

Systems, devices, computer readable media and methods in accordance with the present disclosure are now described more fully hereinafter with reference to the accompanying drawings, where one or more examples are shown. The systems, devices, and methods described herein may be embodied in many different forms and are not to be construed as being limited to the examples set forth herein. Instead, these examples are provided so the disclosure is thorough and complete, and may fully convey the scope of the techniques and devices to those skilled in the art. Each of the systems, devices, media, and methods disclosed herein provides one or more advantages over conventional systems, components, and methods.

FIG. 1 illustrates an exemplary drug delivery system operable to implement the examples disclosed herein.

In some examples, the drug delivery system 100 is suitable for delivering a liquid drug such as insulin to a user in accordance with the disclosed embodiments. The drug delivery system 100 may include a wearable drug delivery device 102, a controller 104 and an analyte sensor(s) 106.

The wearable drug delivery device 102 may be a wearable device that is worn on the body of the user. The wearable drug delivery device 102 may be directly coupled to a user (e.g., directly attached to a body part and/or skin of the user via an adhesive, or the like). In an example, a surface of the wearable drug delivery device 102 may include an adhesive to facilitate attachment to the skin of a user.

The wearable drug delivery device 102 may include a processor 114. The processor 114 may be implemented in hardware, software, or any combination thereof. The processor 114 may, for example, be a microprocessor, a logic circuit, a field programmable gate array (FPGA), an application specific integrated circuit (ASIC) or a microprocessor coupled to a memory. The processor 114 may maintain a date and time as well as be operable to perform other functions (e.g., calculations or the like). The processor 114 may be operable to execute a control application 126 stored in the memory 112 that enables the processor 114 to direct operation of the wearable drug delivery device 102. The control application 126 may control insulin delivery to the user per an AID control approach as describe herein. For example, the control application 126 may be an AID algorithm. The memory 112 may hold settings 124 for a user, such as MDA algorithm settings, such as maximum insulin delivery, insulin sensitivity settings, total daily insulin (TDI) settings, and the like. The memory may also store other data 129, such as total daily insulin values, glucose measurement values from analyte sensor(s) 106 or controller 104, insulin dosage amounts (both basal and bolus) and the like from previous minutes, hours, days, weeks, or months. The analyte sensor(s) 106 may be operable to collect physiological condition data, such as ketone values, ketone values with a time stamp, glucose measurement values (also referred to herein as "glucose values" or "glucose"), glucose measurement values and a timestamp, both ketone values and glucose values that may be shared with the wearable drug delivery device 102, the controller 104, or both. In an additional example, the analyte sensor(s) 106 may include multiple sensors, such as a continuous glucose monitor 186 and a ketone sensor 196. In a further example, the wearable drug delivery device 102 may optionally include a continuous glucose monitor 186A and a ketone sensor 196A, which may be removably incorporated or fully integrated within the wearable drug delivery device 102. For example, the continuous glucose monitor 186A and the ketone sensor 196A may be incorporated in one or more housings 102H of the wearable drug delivery device 102. Note that ketones may also be detected using a breath sensor (which is not shown but may be incorporated in the controller 104) or urine content sensor; however, a subcutaneous ketone sensor gives more accurate information and is more continuous. As described herein, the MDA and AID system is described based on receiving ketone values received subcutaneously. Use of a ketone breath or urine sensor as part of or in addition to the analyte sensor(s) 106106 may delay receipt of the ketone values and modifications to the system 100 may be made.

For example, the communication circuitry 142 of the wearable drug delivery device 102 may be operable to communicate with the analyte sensor(s) 106 and the controller 104 as well as the devices 130, 133 and 134. The communication circuitry 142 may be operable to communicate via Bluetooth, cellular communication, near field communication (NFC), and/or other wireless protocols. While not shown, the memory 112 may include both primary memory and secondary memory. The memory 112 may include random access memory (RAM), read only memory (ROM), optical storage, magnetic storage, removable storage media, solid state storage or the like.

The wearable drug delivery device 102 may include a reservoir 120. The reservoir 120 may be operable to store drugs, medications, or therapeutic agents suitable for automated delivery, such as insulin, morphine, methadone, hormones, glucagon, glucagon-like peptide-1 receptor agonist (GLP-1), glucose-dependent insulinotropic polypeptide (GIP), blood pressure medicines, chemotherapy drugs, combinations of drugs, such as insulin and glucagon-like peptide and/or glucose-dependent insulinotropic polypeptide, or the like. A fluid path to the user may be provided via tubing and a needle/cannula (not shown). The fluid path may, for example, include tubing coupling the wearable drug delivery device 102 to the user (e.g., via tubing coupling a needle or cannula to the reservoir 120). The wearable drug delivery device 102 may be operable based on control signals from the processor 114 to expel the drugs, medications, or therapeutic agents, such as insulin, from the reservoir 120 to deliver doses of the drugs, medications, or therapeutic agents, such as the insulin, to the user via the fluid path. The processor 114 may be operable to cause insulin to be expelled from the reservoir 120.

There may be one or more communications links 128 with one or more devices physically separated from the wearable drug delivery device 102 including, for example, a controller 104 of the user and/or a caregiver of the user and/or a sensor(s) 106. The communication links 128 may include any wired or wireless communication link operating according to any known communications protocol or standard, such as Bluetooth®, NFC, Wi-Fi, a near-field communication standard, a cellular standard, or any other wireless protocol. The analyte sensor(s) 106 may communicate with the wearable drug delivery device 102 via a wireless communication link 131 and/or may communicate with the controller 104 via a wireless communication link 137.

The wearable drug delivery device 102 may also include a user interface 116, such as an integrated display device for displaying information to the user, and in some embodiments, receiving information from the user. For example, the user interface 116 may include a touchscreen and/or one or more input devices, such as buttons, knob(s), or a keyboard that enable a user to provide an input.

In addition, the processor 114 may be operable to receive data or information from the analyte sensor(s) 106 as well as other devices that may be operable to communicate with the wearable drug delivery device 102.

The wearable drug delivery device 102 may interface with a network 108. The network 108 may include a local area network (LAN), a wide area network (WAN) or a combination therein. A computing device 132 may be interfaced with the network, and the computing device may communicate with the insulin delivery device 102. The computing device 132 may be a healthcare provider device through which a user's controller 104 may interact to obtain information, store settings and the like. The AID algorithm operating, as or in cooperation with, the control application 120 may present a graphical user interface on the computing device 132 enabling the input and presentation of information related to the AID algorithm and the example techniques and processes described herein.

The drug delivery system 100 may include an analyte sensor(s) 106 for sensing the levels of one or more analytes of a user. The analyte levels may be used as physiological condition data and be sent to the controller 104 and/or the wearable drug delivery device 102. The sensor(s) 106 may be coupled to the user by, for example, adhesive or the like and may provide information or data on one or more medical conditions and/or physical attributes of the user. The sensor(s) 106 may be a continuous glucose monitor (CGM), a ketone sensor, or another type of device or sensor that provides glucose measurements and/or ketone measurements. The sensor(s) 106 may be physically separate from the wearable drug delivery device 102 or may be an integrated component thereof. The sensor(s) 106 may provide the processor 114 and/or processor 119 with physiological condition data indicative of measured or detected glucose levels of the user. The information or data provided by the sensor(s) 106 may be used to modify a drug delivery schedule and thereby cause the adjustment of drug delivery operations of the wearable drug delivery device 102.

The drug delivery system 100 may also include the controller 104. In the depicted example, the controller 104 may include a processor 119 and a memory 118. The controller 104 may be a special purpose device, such as a dedicated personal diabetes manager (PDM) device. The controller 104 may be a programmed general-purpose device that is a portable electronic device, such as any portable electronic device, smartphone, smartwatch, fitness device, tablet, or the like including, for example, a dedicated processor, such as processor, a micro-processor, or the like. The controller 104 may be used to program or adjust operation of the wearable drug delivery device 102 and/or the sensor(s) 106. The processor 119 may execute processes to control the delivery of the drug or therapeutic agent to the user for the purpose of managing a user's glucose and/or ketone levels. The processor 119 may also be operable to execute programming code stored in the memory 118. For example, the memory 118 may be operable to store a control application 120, such as an AID algorithm, for execution by the processor 119. The control application 120 may be responsible for controlling the wearable drug delivery device 102, including the automatic delivery of drug based on recommendations and instructions from the AID algorithm, such as those recommendations and instructions described herein.

The memory 118 may store one or more applications, such as control application 120, and settings 121 for the drug delivery device 102 like those described above. In addition, the memory 118 may be operable to store other data and/or computer programs 139, such as drug delivery history, glucose and/or ketone measurement values over a period of time, total daily insulin values, and the like. For example, the memory 118 is coupled to the processor 119 and operable to store programming instructions, such as the control application 120 and settings 121, and data, such as other data 139, related to a glucose of a user and/or data related to an amount of insulin expelled by the wearable drug delivery device 102.

The controller 104 may include a user interface (UI) 123 for communicating with the user. The user interface 123 may include a display, such as a touchscreen, for displaying information. The touchscreen may also be used to receive input when it is a touch screen. The user interface 123 may also include input elements, such as a keyboard, button, knob or the like. In an operational example, the user interface 123 may include a touchscreen display (including a display and user input circuitry, such as touch sensitive circuits and the like) controllable by the processor 119 and be operable to present graphical user interfaces and receive inputs via the user input circuitry, the touchscreen display is operable to generate a signal indicative of whether the user is sick (i.e., experiencing an illness) or desires to enter a "sickness mode," as well as, in some example, receive inputs of sickness symptoms, and the like. The touchscreen display, under control of the processor 119, may be operable to, in response to the received input(s), generate a response to a user's drug treatment regimen as well as cause the presentation of prompts on a graphical user interface as described with reference to the later examples described with reference to FIGS. 2A and 3. The graphical user interfaces discussed herein with respect to the later examples may be generated by the processor 119 of the controller 104 and be presented on the UI 123.

The controller 104 may interface via a wireless communication link of the wireless communication links 128 with a network, such as a LAN or WAN or combination of such networks that provides one or more servers or cloud-based services 110 via communication circuitry 122. The communication circuitry 122, which may include transceivers 127 and 125, may be coupled to the processor 119. The communication circuitry 122 may be operable to transmit communication signals (e.g., command and control signals) to and receive communication signals (e.g., via transceivers 127 or 125) from the wearable drug delivery device 102 and the analyte sensor(s) 106. In an example, the communication circuitry 122 may include a first transceiver, such as 125, that may be a Bluetooth transceiver, which is operable to communicate with the communication circuitry 122 of the wearable drug delivery device 102, and a second transceiver, such as 127, that may be a cellular or Wi-Fi transceiver operable to communicate via the network 108 with computing device 132 or with cloud-based services 110.

The cloud-based services 110 may be operable to store user history information, such as glucose measurement values over a set period of time (e.g., days, months, years), a drug delivery history that includes drug delivery amounts (both basal and bolus dosages) and drug delivery times, types of drug delivered, indicated meal times, glucose measurement value trends or excursions or other user-related diabetes treatment information, specific factor settings including default settings, present settings and past settings, or the like.

Other devices, like smart accessory device 130 (e.g., a smartwatch or the like), fitness device 133 and other wearable device 134 may be part of the drug delivery system 100. These devices may communicate with the wearable drug delivery device 102 to receive information and/or issue commands to the wearable drug delivery device 102. These devices 130, 133 and 134 may execute computer programming instructions to perform some of the control functions otherwise performed by processor 114 or processor 119. These devices 130, 133 and 134 may include user interfaces, such as touchscreen displays for displaying information such as current glucose level, ketone level, drug on board (e.g., insulin on board or IOB), drug deliver history, or other parameters or treatment-related information and/or receiving inputs, such as those described with reference to the examples of FIGS. 1-6. The display may, for example, be operable to present a graphical user interface for providing input, such as request a change in basal drug dosage or delivery of a bolus of drug. These devices 130, 133 and 134 may also have wireless communication connections with the sensor(s) 106 to directly receive glucose level data or receive in parallel a presentation of the graphical user interface as shown in FIG. 1.

In another operational example, the controller 104 may be operable to execute programming code that causes the processor 119 of the controller 104 to perform the following functions. The processor 119 of the controller 104 may execute an AID algorithm that is one of the control applications 120 stored in the memory or memory 118. The processor may be operable to present, on a user interface that is at least one component of the user interface 123. The user interface 123 may be a touchscreen display controlled by the processor 119, and the user interface 123 is operable to present a graphical user interface that offers an input of a sickness indication usable by the AID algorithm.

The processor 119 is also operable to collect glucose level and/or ketone level data related to the user from sensors, such as the analyte sensor(s) 106, or heart rate data or body temperature data, for example, from the fitness device 133 or the smart accessory device 130. In an example, the processor 119 executing the AID algorithm may determine a dosage of insulin to be delivered based on the collected physiological condition of the user and a selected list of sickness symptoms. The processor 119 may output a control signal via one of the transceivers 125 or 127 to the wearable drug delivery device 102. The outputted signal may cause the processor 114 to deliver command signals to the pump 118 to deliver the determined dosage of drug from the reservoir 120 to the user. Sickness-related modifications to the AID algorithm settings may be stored in the memory 118, for example, as settings 121.

A wearable drug delivery device 102, typically, has a lifecycle that is based on the amount of liquid drug that is stored in a reservoir 120 of the wearable drug delivery device 102 and/or the amount of the liquid drug delivered to the user. An AID application or algorithm may use a number of parameters, such as glucose measurement values, ketone measurement values, total daily insulin or total daily medicament, drug on board (e.g., insulin on board or IOB), and the like, when making the determination of an amount of the liquid drug to cause to be delivered. In an operational example, the processor 119 of the controller 104 may be operable to receive evaluate the effectiveness of the AID algorithm's control of the drug delivery device 102. For example, the processor 119 may be operable to utilize historical data accessible by the processor in an evaluation of past performance of the AID algorithm and generate recommendations for adjusting settings of the AID algorithm accordingly as described in more detail with reference to the examples of FIGS. 2 and 3).

While the system 100 may be described with reference to delivery of insulin and the use of an AID algorithm, the system 100 may be operable to implement a drug delivery regimen via an automated drug delivery (ADD) or medication delivery algorithm using a number of different liquid or therapeutic drugs. A liquid drug may be or include any drug in liquid form capable of being administered by a drug delivery device via a subcutaneous cannula, including, for example, insulin, glucagon-like peptide-1 (GLP-1), glucose-dependent insulinotropic polypeptide (GIP), pramlintide, glucagon, co-formulations of two or more of GLP-1, GIP, pramlintide, and insulin; as well as pain relief drugs, such as opioids or narcotics (e.g., morphine, or the like), methadone, blood pressure medicines, chemotherapy drugs, fertility drugs, or the like.

In an example executable by the AID system 100, a processor may be operable to execute programming code that implements an algorithm that adapts insulin delivery for sick days and safety monitoring. At a high level, the processor may be operable to receive and adapt to a sickness announcement, and provide ketone monitoring, drug delivery adaptation, and safety alerts. With a sickness or a sick day announcement, a user interface on a portable diabetes manager (PDM), such as controller 104 of FIG. 1, may enable the user to indicate that today is a sick day (or trigger initiation (or deactivation) of a sickness mode) and may be provided with sub menus to describe specific attributes of the sickness. The indication of sickness for pediatric users is particularly helpful as their metabolisms are more affected by the symptoms of sickness, such as fever, nausea, vomiting, and diarrhea.

Examples of drug delivery adaptation may include adapting basal and bolus insulin delivery based on the indicated sickness symptoms. The algorithm enables the processor to address symptomatic hyperglycemia and hypoglycemia avoidance. The processor while executing the algorithm may be operable to generate safety alerts for impending DKA, hypoglycemia, or hyperglycemia, and may be operable to generate notifications that the user should get medical attention based on the indicated sickness, glucose level measurements, ketone level measurements, and ability (or inability) of the system to adapt drug delivery to the user's condition.

Figure 2A:
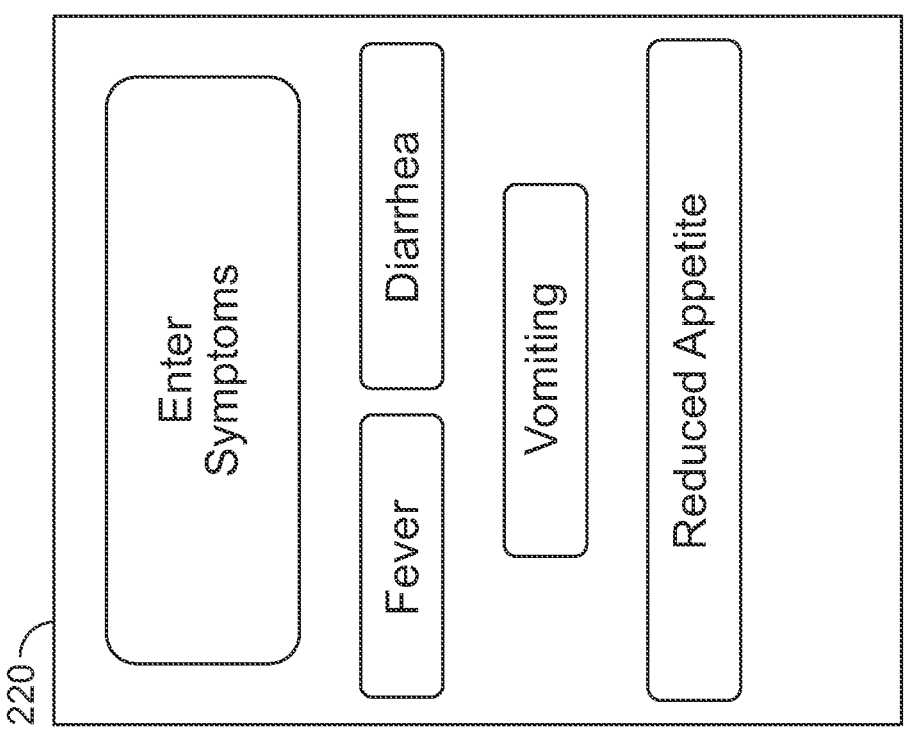
FIG. 2A illustrates a block diagram of an exemplary graphical user interface operable to receive an indication to enter a sickness mode (e.g., a "sick day mode") (or turn off a sickness or sick day mode), and may also receive input of one or more symptoms of an illness in the same menu or in a submenu.
Figure 2A:
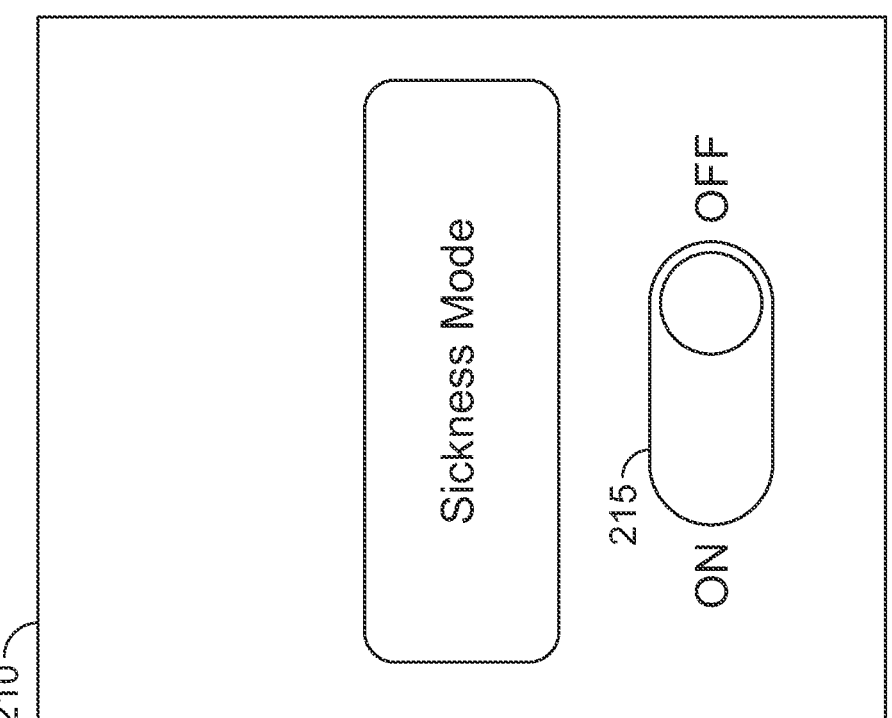

In more detail with regard to initiation of a sickness mode, the processor may be operable to provide a graphical user interface through which the user may indicate sickness. FIG. 2A illustrates a block diagram of a graphical user interface operable to receive an indication that the user is feeling sick and desires to enter a sickness mode (or deactivate a sickness mode), and may also be operable to receive one or more symptoms of an illness.

With sickness, a fever may cause higher glucose and hence a greater risk of hyperglycemia. In contrast, if the PWD is unable to keep food and fluids in their digestive system due to vomiting or diarrhea, or is unable to eat due to nausea, the user has the risk of becoming hypoglycemic. These situations may be monitored via sensing of blood glucose levels and/or ketone levels.

In the FIG. 2A example, a user may be presented with a GUI window, such as 210, that enables the user to initiate (or deactivate) sickness mode by touching a button labeled "sickness mode." Additionally, or alternatively, the GUI window 210, may have a toggle button 215, which the user may use to toggle the sickness mode on and off. After initiation of sickness mode via the GUI window 2A, the user may be prompted to input symptoms of sickness that may include fever, vomiting, diarrhea, decreased appetite as presented in a GUI window such as 220. For a new sickness invocation, the user may have the option of entering the recency of the symptom.

Figure 2B:
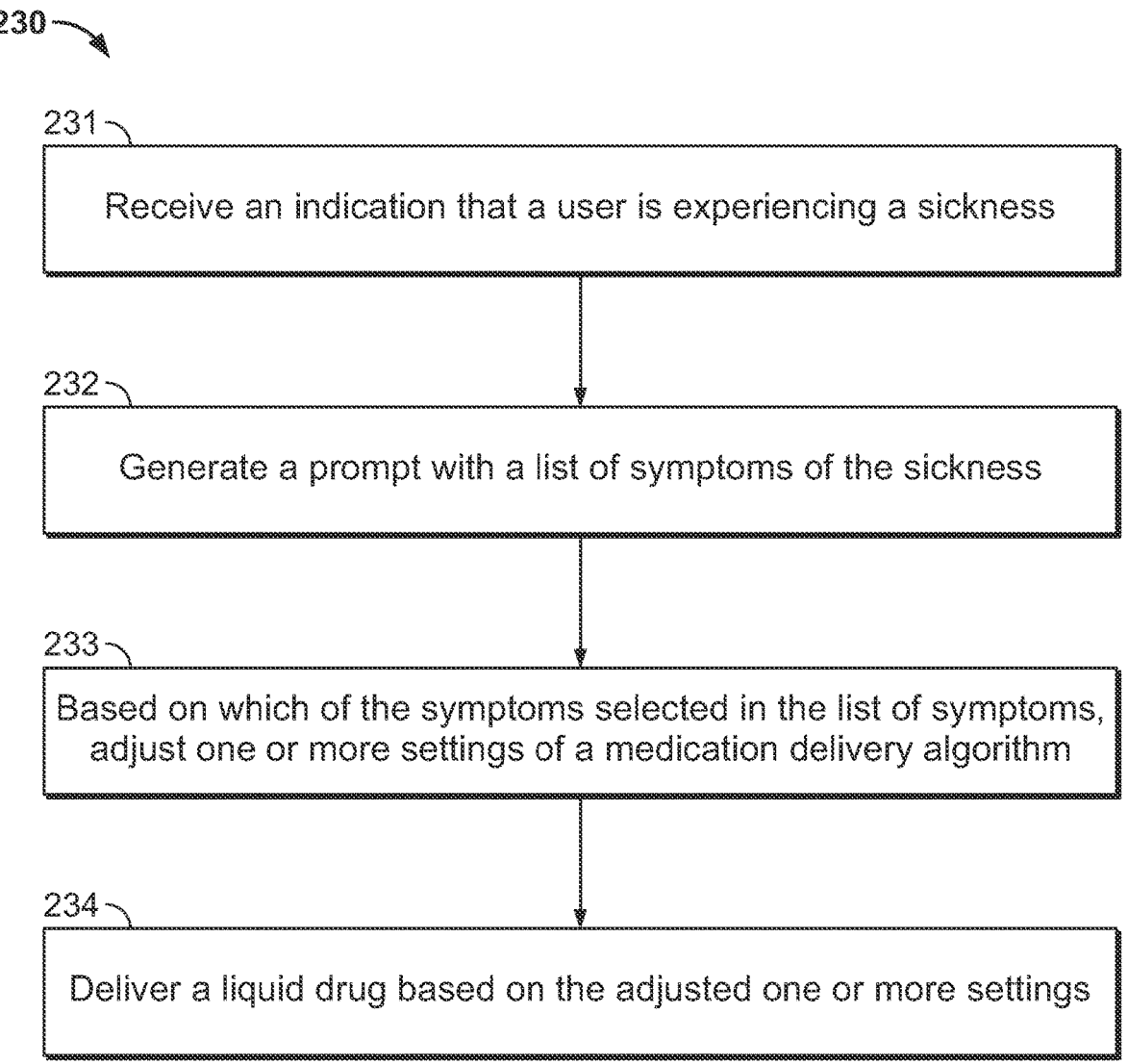
FIG. 2B illustrates an exemplary process that utilizes a sickness mode indication and the symptom inputs from a graphical user interface such as the graphical user interface described with reference to FIG. 2A.

FIG. 2B illustrates an exemplary process that incorporates the user interface described with reference to FIG. 2A. In an operational example, a controller of a drug delivery system that may include a processor, a user interface including a display and user input circuitry, a memory and communication circuitry may be operable to perform a process that provides the GUI windows 210 and 220 and also makes adjustments to a medication delivery application. In the example, the processor operable to receive and transmit wireless communication signals, as well as inputs via the graphical user interface presented on the display of the user interface. In the exemplary process 230, the processor is operable to receive a sickness mode indication (231) that a user is ill and is experiencing a sickness.

The processor may generate a prompt with a list of symptoms of sicknesses at 232. Each symptom in the list of symptoms may be presented and selectable by the user. For example, the GUI may present a list such as fever, vomiting, diarrhea, nausea, reduced appetite, or the like. The list of symptoms may be those that are the result of raised ketone levels, lower glucose levels, higher glucose levels, dehydration, or the like. At 233, the processor executing a medication delivery algorithm may be operable to adjust one or more settings of the medication delivery algorithm based on which of the symptoms were selected in the list of symptoms. For example, a setting for total daily insulin, a correction factor for insulin sensitivity, basal delivery rate, basal dosage level, bolus dosage level, and the like may be adjusted depending upon the selected symptom or selected combination of symptoms. The processor may be further operable to deliver a liquid drug based on the adjusted one or more settings (234).

Typically, the AID algorithm may adapt insulin delivery based on previous user histories (e.g., glucose levels, insulin deliveries, ketone level histories, or the like); however, due to the sick day announcement by the user, the AID algorithm may suspend its typical performance, or may not utilize while in sickness mode data (e.g., glucose levels, insulin delivery history, ketone level history, or the like) collected during the time period prior to when the user initiated sickness mode, or may not utilize data (e.g., glucose levels, insulin delivery history, ketone level history, or the like) collected while in sickness mode for adjusting settings when not in sickness mode. Data collected while in or not in sickness mode may be separated and primarily used for algorithm adjustments while in the particular mode (i.e., while in or not in sickness mode). Not utilizing the data collected while in one mode (e.g., during sickness mode) for another mode (e.g., while not in sickness mode), prevents the AID algorithm from skewing settings based by commingling in memory data collected on sick days (or while in sickness mode) with measurements and data collected when the user was not experiencing a sick day (or was not in sickness mode).

Figure 3:
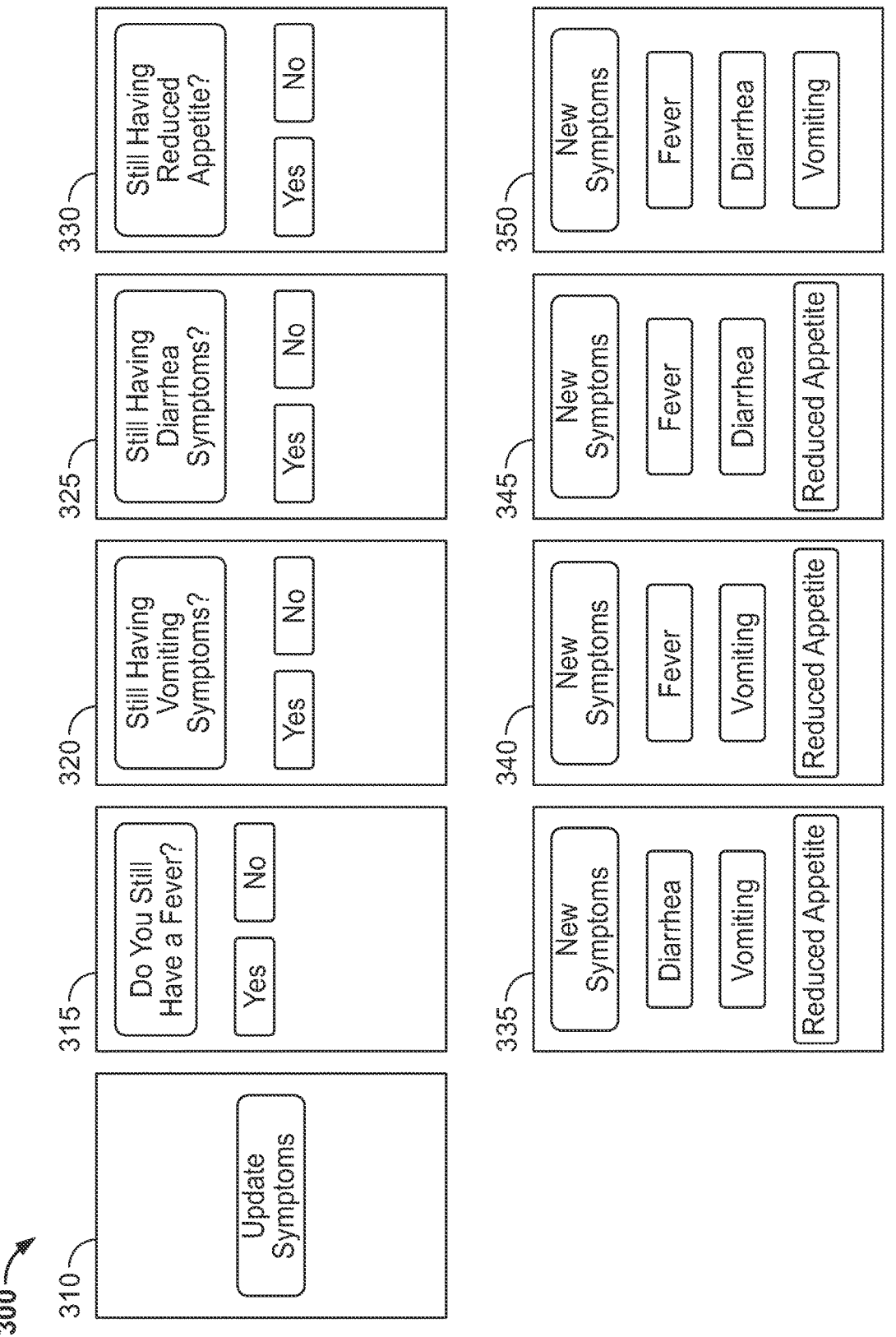
FIG. 3 illustrates a block diagram of an exemplary graphical user interface as described herein.

The processor upon receipt of the inputted symptoms, may at a later time (which may be a user-chosen time interval (for example, every 4-6 hours, 12 hours, 24 hours, or the like)) generate another prompt for an update of the symptoms of the sickness as shown in the example of FIG. 3. FIG. 3 shows exemplary GUI windows for inquiring about a user's sickness and updating the user's symptoms. Additionally or alternatively, the processor may, at a later time (which may also be a user-chosen time interval or a default time interval (for example, every 12 hours, 24 hours, or the like)) generate a prompt for the user to confirm that "sickness mode" should still be activated, e.g., for the user to confirm whether they are still experiencing a sickness or symptoms. If the user deactivates "sickness mode" via a GUI, the processor may revert the MDA settings back to the usual or non-sickness mode settings for the user.

As shown in the sick day symptoms update GUI 300 of FIG. 3, different GUI windows 310 through 350 of the sick day symptoms update GUI 300 may be presented to the user to enable the user to update the medication delivery algorithm with their symptoms. The user's guardian, when the PWD is a child, for example, may respond to the inquires. The different GUI screens 310-350 may be presented in the order shown, or another order, to enable the user to easily update the MDA with the user's previous symptoms as well as add any new symptoms.

In an example, the initial symptoms entered in GUI window 220 of FIG. 2A may be stored in memory. The processor executes programming code that causes the processor to inquire with the user whether the previously selected and stored symptoms persist by presenting GUI windows 315, 320, 325 and 330. The update symptoms sick day GUI window 310 may be presented by the processor to periodically request that the user update the MDA as shown in FIG. 3. The processor may produce the update symptoms sick day GUI window 310 after the initial indication that the PWD is experiencing a sick day. For example, after receiving the initial indication and making adjustments to the MDA settings, the processor may start a timer or the like that signals a set period of time, such as 4-6 hours, 8-10 hours, 12-24 hours, or the like. After the set period of time, the processor may execute programming code that causes the processor to generate a GUI window, such as 310 that begins a query session that enables the user's (also referred to as PWD herein) initially selected symptoms to be updated.

Receiving updates via the GUI windows 310-350 allows the MDA to make additional adjustments to MDA settings because, for example, prolonged episodes of vomiting, diarrhea, and reduced food intake can contribute to hypoglycemia. Additionally, in some examples, a user's insulin needs usually increase when they are experiencing a fever (e.g., a body temperature of 100.4 degrees or greater). In children, vomiting is also often attributed to insulin deficiency which in turn may be contributing to higher ketone levels, the higher ketone levels may increase nausea and affect other symptoms, such as decreased appetite. Decreased appetite may lead to low carbohydrate ingestion which can also increase ketone levels. When a user has been vomiting and experiencing diarrhea, their ketone levels may rise which if the sickness is severe or prolonged may potentially put the user at risk of DKA.

Therefore, as part of the sickness mode symptoms update GUI 300 to the medication delivery application, a GUI window 315 may be presented to inquire whether the user is still experiencing a fever. After the GUI window 315 receives an input, the processor may generate additional GUI windows to receive specific symptom updates.

The GUI 300 may present individual windows 320, 325 and 330 to cover existing symptoms as well as any new symptoms. To narrow down the needed adjustments to the MDA, the processor may present GUI window 320 to confirm whether the user is still experiencing symptoms of nausea or vomiting, GUI window 325 to confirm whether the user is still experiencing symptoms of diarrhea, and GUI window 330 to confirm whether the user has a reduced appetite.

New symptoms can be entered (e.g., via GUI windows 335, 340, 345, and 350). The GUI windows 335, 340, 345, and 350 may offer a number of combinations of new symptoms For example, while the GUI windows 315, 320, 325 and 330 may be used to confirm previous selected symptoms or if the user had the symptom previously, GUI windows 335, 340, 345 and 350 offer the user the opportunity to enter new symptoms. In an example, not all of the GUI windows 335, 340, 345 and 350 need to be presented. Alternatively, a single GUI window may be presented with all of the symptoms listed for selection. If all of the responses to windows 315, 320, 325 and 330 are "No" and no new symptoms are entered, the MDA may be operable to determine that the sickness has been resolved. Based on the determination that the sickness has been resolved, the processor may revert the MDA settings back to the usual settings for the user. For example, the user may have a non-sickness mode TDI setting, a non-sickness mode basal dosage setting, a non-sickness mode basal rate setting, a non-sickness mode bolus delivery dosage setting, or the like, and the processor may be operable to revert to those non-sick day settings.

Ketone monitoring in pediatric diabetes patients may be slightly different than the ketone monitoring discussed above.

Ketone levels are typically <0.6 mmol/L for pediatric diabetic patients. Ketone levels increase under low carbohydrate diets and starvation. In the context of sick days, these same conditions (e.g., low carbohydrate intake and increased ketone levels) can arise from symptoms of vomiting, reduced appetite, and dehydration from diarrhea.

Ketones are produced by the liver from free fatty acids that are mobilized as an alternative energy source when there is a lack of glucose for intracellular metabolism. This can happen either because of insulin insufficiency or inadequate intake of carbohydrates. Starvation ketones are produced when the glucose is low. Ketones accumulate because of increased lipolysis (i.e., the breakdown of fats and other lipids by hydrolysis to release fatty acids) and increased ketogenesis (i.e., the production of ketone bodies during the metabolism of fats) due to low insulin levels and elevated counter regulatory hormones, such as cortisol, glucagon, adrenaline, and growth hormone. As a result, the increase in ketone levels may exacerbate the sick person's (especially a child's) lack of appetite by causing nausea, which in turn causes a further increase in ketone levels.

In an example, MDA systems may be equipped with a continuous subcutaneous ketone sensor, such as analyte sensor(s) 106 of FIG. 1. Concentration of 3-hydroxybutyrate can be measured using the 3-hydroxybutyrate dehydrogenase (3HBDH) enzyme which can be integrated with the CGM sensor, such as analyte sensor(s) 106 of FIG. 1. Hydrogel membranes have been used to improve ketone concentration and reduce electrode fouling. Ketone levels of pediatric diabetic patients are summarized in the Chart 1 below:

CHART 1

| Serum Ketone Levels. | |
| --- | --- |
| Ketone Level labels | Ketone Level |
| Negative | 0-0.6 mmol/L |
| Trace | 0.6-0.9 mmol/L |
| Small/Moderate | 1.0-1.4 mmol/L |
| Moderate/Large | 1.5-2.9 mmol/L |
| High | $>_3$ mmol/L |

In some examples, the ketone sensor and the CGM sensor may be integrated within the insulin delivery system as one physical unit or may be separate sensors configured to fit together or physically connect to one another in one or more housings. In other examples, serum ketone levels/urine ketone levels may be measured every 2 to 4 hours using non-wearable sensors. In the case of urine ketone levels, only qualifiers 'negative,' 'trace,' 'small,' 'moderate' and 'large' (the numerical ketone concentrations in urine will be different) may be used for insulin adaptation and oral fluid hydration recommendations.

Insulin adaptation may occur when both basal and bolus insulin needs change depending on the combination of glucose values and ketone levels. We consider the case of hyperglycemia first and then normoglycemia/hypoglycemia next.

In cases of hyperglycemia or potential hyperglycemia, the algorithm may be programmed to assume baseline basal and bolus deliveries to be as follows:

Basal Delivery: The basal rate (i.e., the amount of insulin delivery via a basal dosage per hour or another time period) depends on the Total Daily Insulin (TDI) and a split factor as shown below Equation 1):

$$\text{Basal rate} = \frac{\text{Total Daily Insulin} * BasalBolus \text{ Split Factor}}{24}$$

where 24 is the number of hours in a day, and the basal/bolus split factor is a percentage (e.g., 50%, 40% or 60%) that divides the TDI into basal and bolus portions. The basal portion and the bolus portion are the parts of the TDI that are the percentages of the TDI that is delivered via basal delivery (e.g., a continuous dosage that may fluctuate according to time of day) and bolus delivery (e.g., an amount used to compensate for meals and/or for correction).

Bolus Delivery: The bolus amount determined according to the bolus delivery equation below may be delivered as fraction of the Total Daily Insulin (TDI) and a correction term which is proportional to the deviation of the glucose from the setpoint divided by the Correction Factor (CF). The CF can be taken as either the 1800 or 1600 Rule. According to the Bolus delivery equation, bolus insulin amount may be determined by (Equation 2):

$$\text{Bolus Insulin} = x * TDI + \frac{BG - (\text{setpoint} + \text{elevation})}{CF} - IOB$$

where x may be a tunable number for an individual and may typically vary from 6% to 12% and may vary with the time of the day.

In an example, a hybrid closed-loop controller may also modulate insulin delivery on top of the nominal basal delivery rate based on AID system constraints, predicted glucose values and the current Insulin on Board (IOB). The revised TDI allows the AID system to increase or decrease insulin delivery on a sick day or when in sickness mode, and does not influence the TDI when the sickness has resolved or when not in sickness mode. FIG. 4 presents a flowchart of an exemplary process utilizing ketone measurement values to modify medication delivery algorithm settings. The process 400 illustrated in FIG. 4 may utilize the responses in the following charts to modify the medication delivery algorithm settings to address the possibilities of hyperglycemia, normoglycemia, and hypoglycemia.

In the example process 400, a processor of a closed-loop controller, which may also be a hybrid closed-loop controller, may be operable to receive a sickness indication that a user is experiencing a sickness. For example, the processor, at 410, may be operable to receive the sickness indication via a connection to the GUI windows presented in the examples illustrates in FIGS. 2A and 3. The received sickness indication may be only the indication that the user is experiencing a sickness. Additionally, or alternatively to only the received indication, the received indication may include a list of sickness symptoms that the user is experiencing. In addition to the received indication and/or the list of sickness symptoms, the received indication may include updated symptom indications, such as those shown in GUI windows 315, 320, 325 and 330 of FIG. 3 and/or new symptom indications, such as those shown in GUI windows, 335, 340, 345 and 350 of FIG. 3. The processor at 420 may be further operable to receive, via communication circuitry coupled to the processor, a ketone measurement value from a ketone sensor, such as 196 or 196A of FIG. 1. At 430, the processor may also be operable to receive, via the communication circuitry, a glucose measurement value from a glucose monitor, such as 186 or 186A of FIG. 1.

The processor using the received glucose measurement value may be operable to further determine whether the received glucose measurement value is within a predetermined glucose value range. Stored in the memory may be look up tables or other data structures, or computer routines, which implement changes as identified, for example, in the tables below (e.g., Table 1, Table 2).
Hyperglycemia (Table 1)

Hyperglycemia in sickness may primarily stem from fever and/or insulin deficiency as well as dehydration (which may be caused by vomiting, diarrhea, and/or loss of appetite). The processor by evaluating the received glucose measurement values and the ketone measurement values may be operable to implement the following recommendations.

Hyperglycemia may be evaluated by the processor with reference to different ketone values as shown in Table 1 below:

TABLE 1

| 180 < BG < 250 mg/dL | 250 < BG < 400 mg/dL |
|---|---|
| Negative for Ketones: ketone level < 0.6 mmol/L | |
| No specific action | Increase TDI by 5% This increases nominal basal by 5%. Bolus delivery increased as given by the Bolus Delivery Equation above |
| Trace Ketones: 0.6 mmol/L < ketone level < 0.9 mmol/L | |
| Increase TDI by 5% This increases nominal basal by 5% Bolus delivery increased as given by the Bolus Delivery Equation above | Increase TDI by 7.5% This increases nominal basal by 7.5%. Bolus delivery increased as given by the Bolus Delivery Equation above |

TABLE 1-continued

| 180 < BG < 250 mg/dL | 250 < BG < 400 mg/dL |
| --- | --- |
| Small/Moderate Ketone Level: 1.0 mmol/L < ketone level < 1.4 mmol/L | |
| Increase TDI by 7.5%<br>This increases nominal basal by 7.5%<br>Bolus delivery increased as given by<br>the Bolus Delivery Equation above | Increase TDI by 10%<br>This increases nominal basal by 10%.<br>Bolus delivery increased as given by<br>the Bolus Delivery Equation above |
| Moderate/Large Ketones Level: 1.5 mmol/L < ketone level < 2.9 mmol/L | |
| Increase TDI by 10%<br>This increases nominal basal by 10%<br>Bolus delivery increased as given by<br>the Bolus Delivery Equation above | Increase TDI by 20%<br>This increases nominal basal by 20%.<br>Bolus delivery increased as given by<br>the Bolus Delivery Equation above |

High Ketones: ketone level > 3.0 mmol/L
Same Action as Moderate/Large Ketones.
DKA Alert In the example of process 400, the processor may evaluate the received glucose measurement values against the number of exemplary glucose value ranges in Table 1 and Table 2 (below). Table 1 provides responses for glucose measurement values that are in a hyperglycemic threshold range. A hyperglycemic threshold range may be a glucose measurement value range has as a minimum of 180 mg/dL. The hyperglycemic threshold range may be further subdivided into a first blood glucose value range and a second blood glucose value range. In Table 1, there are a first (hyperglycemic) blood glucose (BG) value range (i.e., 180 mg/dL<BG<250 mg/dL) and a second (hyperglycemic) blood glucose (BG) value range (i.e., 250 mg/dL<BG<400 mg/dL). Table 2 provides responses for glucose measurement values that are in a hypoglycemic threshold range and a normoglycemic threshold range. As a result, Table 2 has a threshold range for different blood glucose states (i.e., hypoglycemic and normoglycemic). In the example, and in the context of sick day management, the hypoglycemic threshold range may be a glucose measurement value range has as a maximum of 90 mg/dL, while the normoglycemic threshold range may have a maximum of 180 mg/dL. As shown in Table 2 below, there are a first (hypoglycemic) blood glucose (BG) value range (i.e., BG<90 mg/dL) and a second (normoglycemic) blood glucose (BG) value range (i.e., 90 mg/dL<BG<180 mg/dL).

At 440, the processor may determine whether the received glucose measurement value is within a predetermined blood glucose value range. For example, the processor may be operable to determine whether the glucose measurement value is within either the first BG value range or the second BG value range.

At 450, in addition to using the determination of whether the received glucose measurement is within a predetermined blood glucose value range, the processor may also evaluate the received ketone measurement value against a number of different ketone level thresholds or ranges. For example, as shown in Table 1, a first ketone level threshold may be less than 0.6 mmol/liter (L) (this first ketone level threshold may also be referred to as "negative for ketones"), a second ketone level threshold may be a range of 0.6 mm/L to 0.9 mmol/L (that is also referred to as "trace ketone level"), a third level threshold may be a range of 1.0 mm/L to 1.4 mmol/L (that is also referred to as "small/moderate ketone level"), a fourth ketone level threshold may be a range of 1.5 mm/L to 2.9 mmol/L (that is also referred to as "moderate/large ketone level"), and a fifth ketone level threshold may be a ketone level greater than 3.0 mmol/L (that is also referred to as "high ketone level").

In the example, after determining the blood glucose value range and the ketone threshold range in which the received ketone measurement value fits as shown in the respective Tables 1 or 2, the processor, continuing to execute programming code at 450 may modify one or more medication delivery algorithm settings as shown in the respective table under use. For example, assume the glucose measurement value is 220 mg/dL and a ketone measurement value of 0.7 mmol/L. The processor may determine that the user's ketone measurement value is a trace ketone level and that the glucose measurement value of 220 mg/dL is within the first blood glucose (BG) value range of 180 to 250 mg/dL. Accordingly, the processor may modify the medication delivery algorithm setting of the user's total daily insulin (TDI) by increasing the user's TDI by 5% of the current TDI setting.

Of course, other values of the glucose measurement values or ketone measurement values may be evaluated by the processor and other responses as indicated in Table 1 (above) and Table 2 (below).

Normoglycemia/Hypoglycemia (Table 2)

Hypoglycemia may occur under conditions of vomiting, diarrhea, reduced appetite leading to reduced food intake. Insulin adaptation for normoglycemia/hypoglycemia is depicted below. The basal and bolus insulin dosages are changed based on changing the TDI. The algorithm delivery by the closed loop AID system will modulate the basal delivery based on current BG and predicted BG values and the IOB.

TABLE 2

| BG < 90 mg/dl | 90 < BG < 180 mg/dl |
| --- | --- |
| Negative for Ketones: ketone level < 0.6 mmol/L | |
| Reduce TDI by 20%<br>This reduces nominal basal by 20%.<br>If BG drops below 70 mg/dl suspend | No specific action |

TABLE 2-continued

| BG < 90 mg/dl | 90 < BG < 180 mg/dl |
|---|---|
| insulin delivery Bolus delivery decreased as given by the Bolus Delivery Equation | |
| Trace Ketones: 0.6 mmol/L < ketone level < 0.9 mmol/L | |
| Reduce TDI by 15% This reduces nominal basal by 15% Bolus delivery decreased as given by the Bolus Delivery Equation | No specific Action |
| Small/Moderate Ketone Level: 1.0 mmol/L < ketone level < 1.4 mmol/L | |
| TDI remains same as Baseline | No Specific Insulin adjustment |
| Moderate/Large Ketones Level: 1.5 mmol/L < ketone level < 2.9 mmol/L | |
| TDI remains same as Baseline | Increase TDI by 5% This increases nominal basal by 5%. Bolus delivery increased as given by the Bolus Delivery Equation |

High Ketones: ketone level > 3 mmol/L
Same Action as Moderate/Large Ketones.
DKA Alert Returning to the process 400 of FIG. 4, after modifying the medication delivery algorithm setting at 450, where the medication delivery algorithm setting in this example is TDI, the process 400 may proceed to 460.

At 460, the processor may use the modified medication delivery algorithm to determine an adjustment in medication delivery. Returning to the example of the modifying the TDI (i.e., the medication delivery algorithm setting) by 5%, the processor may use the user's TDI to increase the user's nominal or baseline basal dosage by 5% and the user's bolus dosage would be increased as given by the bolus delivery equation (i.e., Equation 2 labeled "bolus insulin").

The medication delivery algorithm executed by the processor may be operable to continue to evaluate the user's glucose measurement values and ketone measurement values on a continuing basis (e.g., 1 minute, 5 minutes (which is a time period for an operational cycle of a drug delivery device, 10 minutes, 90 minutes, or the like). The modified medication delivery algorithm setting may remain modified until the glucose measurement values fall out of the ranges listed in the tables (e.g., Tables 1 and 2) or the ketone measurement values fall out of the ranges listed in the tables (e.g., Tables 1 and 2). In this example, the TDI increases may remain active for the next 6 hours after modification and be revaluated at the end of that time period based on subsequent glucose measurement values and ketone measurement values, and/or updated sickness symptoms as indicated via GUI windows of FIG. 2.

In a further example of the diabetes treatment regime improvements provided herein, the processor may control the user interface to also present GUI windows (not shown) that provide the user with oral intake alerts. For example, depending on the glucose measurement values and ketone measurement values, the user interface can also prompt the user to ingest fluids (e.g., sugary fluids or non-sugary fluids) and/or extra carbohydrates. The oral intake alerts are outlined below with respect to hyperglycemic and normoglycemic/hypoglycemic conditions and may take the form of messages such as "Hydrate with sugar free fluids," "Hydrate with sugary fluids," "Hydrate with sugar free fluids," "Ingest extra carbohydrates," a combination of these, or the like. In cases where the glucose measurement value is not within either the first range or the second range, the processor may take no specific action. Depending upon the received sickness indication and a list of selected symptoms as well as the received glucose measurement values and ketone measurement values, the alerts may be provided every 4-6 hours when the sickness symptoms are being updated, or another time period.

Similar to the process of FIG. 4, a process as shown in FIG. 5 may be implemented to provide the user with the oral intake alerts.

In the example process 500, a processor of a closed-loop controller, which may also be a hybrid closed-loop controller, may be operable to receive a sickness indication that a user is experiencing a sickness. For example, the processor, at 510, may be operable to receive the sickness indication via a connection to the GUI windows presented in the examples illustrates in FIGS. 2A and 3. The received sickness indication may be only the indication that the user is experiencing a sickness. Additionally, or alternatively to only the received indication, the received indication may include a list of sickness symptoms that the user is experiencing. In addition to the received indication and/or the list of sickness symptoms, the received indication may include updated symptom indications, such as those shown in GUI windows 315, 320, 325 and 330 of FIG. 3 and/or new symptom indications, such as those shown in GUI windows, 335, 340, 345 and 350 of FIG. 3. The processor at 520 may be further operable to receive, via communication circuitry coupled to the processor, a ketone measurement value from a ketone sensor, such as 196 or 196A of FIG. 1. At 530, the processor may also be operable to receive, via the communication circuitry, a glucose measurement value from a glucose monitor, such as 186 or 186A of FIG. 1.

The processor using the received glucose measurement value may be operable to further determine whether the received glucose measurement value is within a predetermined blood glucose value range. Stored in the memory may be look up tables or other data structures, or computer routines, which implement changes as identified, for example, in the tables below (e.g., Table 3, Table 4).

In the example of process 500, the processor may evaluate the received glucose measurement values against the number of blood glucose value ranges in Table 3. In Table 3 (Hyperglycemia Oral Intake Alerts), there are a first blood glucose (BG) value range (i.e., 180<BG<250 mg/dL) and a second blood glucose (BG) value range (i.e., 250<BG<400 mg/dL). At 540, the processor may determine whether the received glucose measurement value is within a predetermined blood glucose value range. For example, the processor may be operable to determine whether the glucose measurement value is within either the first BG value range or the second BG value range.

At 550, in addition to using the determination of whether the received glucose measurement is within a predetermined blood glucose value range, the processor may also evaluate the received ketone measurement value against a number of different ketone level thresholds or ranges. For example, as shown in Table 1, a first ketone level threshold may be less than 0.6 mmol/liter (L) (this first ketone level threshold may also be referred to as "negative for ketones"), a second ketone level threshold may be a range of 0.6 mm/L to 0.9 mmol/L (that is also referred to as "trace ketone level"), a third level threshold may be a range of 1.0 mm/L to 1.4 mmol/L (that is also referred to as "small/moderate ketone level"), a fourth ketone level threshold may be a range of 1.5 mm/L to 2.9 mmol/L (that is also referred to as "moderate/large ketone level"), and a fifth ketone level threshold may be a ketone level threshold greater than 3.0 mmol/L (that is also referred to as "high ketone level").

Based on into which ketone level threshold (first through fifth) the ketone measurement value falls, the processor may cause the generation of a respective oral intake alert on the GUI. The generated oral intake alert may present one or more of the messages presented in the Tables 3 and 4 below.

Hyperglycemia Oral Intake Alerts (Table 3)

TABLE 3

| 180 < BG < 250 mg/dL | 250 < BG < 400 mg/dL |
|---|---|
| Negative for Ketones: ketones level < 0.6 mmol/L | |
| No specific action | Hydrate with sugar free fluids |
| Trace Ketones: 0.6 mmol/L < ketone level < 0.9 mmol/L | |
| Hydrate with sugar free fluids | Hydrate with sugar free fluids |
| Small/Moderate Ketone Level: 1.0 mmol/L < ketone level < 1.4 mmol/L | |
| Hydrate with sugar fluids Ingest extra carbs | Hydrate with sugar free fluids |
| Moderate/Large Ketones Level: 1.5 mmol/L < ketone level < 2.9 mmol/L | |
| Hydrate with sugar fluids Ingest extra carbs | Hydrate with sugar free fluids |

High Ketones: ketone level > 3 mmol/L
Same Action as Moderate/Large Ketones.
Generate a DKA Alert Normoglycemia/Hypoglycemia Oral Intake Alerts (Table 4)

TABLE 4

| BG < 90 mg/dl | 90 < BG < 180 mg/dl |
|---|---|
| Negative for Ketones: ketone level < 0.6 mmol/L | |
| Oral sugary fluids Extra carbs | No specific action |
| Trace Ketones: 0.6 mmol/L < ketone level < 0.9 mmol/L | |
| Oral sugary fluids Extra carbs | Oral sugary fluids Extra carbs |
| Small/Moderate Ketone Level: 1.0 mmol/L < ketone level < 1.4 mmol/L | |
| Oral sugary fluids Extra carbs | Oral sugary fluids Extra carbs |

TABLE 4-continued

| BG < 90 mg/dl | 90 < BG < 180 mg/dl |
|---|---|
| Moderate/Large Ketones Level: 1.5 mmol/L < ketone level < 2.9 mmol/L | |
| Oral sugary fluids Extra carbs | Oral sugary fluids Extra carbs |

High Ketones: ketone level > 3 mmol/L.
Same Action as Moderate/Large Ketones for BG < 90 mg/dl.
Oral sugar fluids and extra carbs not needed when 90 < BG < 180 mg/dl
DKA Alert FIG. 6 illustrates an exemplary process for utilizing data learning to make modifications to a blood glucose prediction model. In the data driven learning process 600, the processor may receive inputs or retrieve data to the sickness symptom(s) or label(s) from a user interface or a memory at 610. For example, the process 600 may retrieve the sickness symptoms shown in FIG. 3. The processor may also receive inputs via a GUI window or retrieve data from memory, such as a ketone measurement value history, at 612 and at 614, retrieve data from memory, such as a glucose measurement value history. The processor may be further operable to retrieve from the memory, at 616, an insulin delivery history.

Each of the respective histories, the ketone measurement value history, the glucose measurement value history, and the insulin delivery history may track over the same time period, such as 12 hours, 72 hours, 96 hours, 7 days, two weeks, or the like. The number of data points for each of the respective measurement values and insulin deliveries may differ over the time period. For example, glucose levels may be measured more frequently than ketone levels are measured during a same period of time, and insulin may be delivered at separate times than when glucose is measured during a same period of time.

The processor may opportunistically use the data retrieved from the respective histories to improve a blood glucose prediction model by inputting the data retrieved in steps 612, 614 and 616 into a blood glucose prediction model (618). This extensive amount of data is likely to improve patient outcomes by minimizing errors in the prediction model. For example, in the above framework for blood glucose prediction, sickness labels, glucose history, ketone measurement values, ketone threshold levels, glucose measurement values, and reference glucose values may be used as inputs to the processor and are provided to a blood glucose prediction model to predict future glucose values. The blood glucose prediction model may use the various inputted data to generate a prediction of a user's glucose measurement value. This predicted glucose measurement value may be output and used by the MDA algorithm to change various settings including drug delivery settings, and the like.

Additionally, at 620, the processor may be operable to determine an adjustment in delivery of medication according to the output of the blood glucose prediction model. For example, the processor executing the MDA algorithm may be operable to calculate a delivery dosage for a next basal delivery, a calculation of TDI, or the like.

Typical configurations for time series learning, for example, recurrent neural networks can be used to build the blood glucose prediction model. Of course, other neural network types may be used, such as feed forward networks, multi-layer perceptron networks, radial based networks, convolutional neural networks, and/or long- or short-term neural network. Individualized blood glucose prediction models can be tuned from the population model using transfer learning, which is a supervised learning technique that reuses parts of a previously trained model on a new network tasked for a different but similar problem. The individualized blood glucose prediction models may be used to improve patient outcomes, for example, when using the sick mode. The outputs of the blood glucose prediction model may be analyzed with reference blood glucose values and any errors may be minimized via a process 600. Error minimizing factors may be provided by another function executed by the processor and provided to the blood glucose prediction model to optimize the prediction model. The foregoing process 600 may be done at the population level for generalized models and adapted for the individual for a personalized model.

Software related implementations of the techniques described herein, such as the processes examples described with reference to the above discussion and figures may include, but are not limited to, firmware, application specific software, or any other type of computer readable instructions that may be executed by one or more processors. The computer readable instructions may be provided via non-transitory computer-readable media. The various elements of the processes described with reference to the figures may be implemented in devices, apparatuses or systems that may include various hardware elements, software elements, or a combination of both. Examples of hardware elements may include structural members, logic devices, components, processors, microprocessors, circuits, processors, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, processes, procedures, software interfaces, application program interfaces (API), instruction sets, computing code, computer code, code segments, computer code segments, words, values, symbols, or any combination thereof.

Some examples of the disclosed device or processes may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but the intention is that additions and modifications to what was expressly described herein are also included within the scope of the disclosed examples. Moreover, it is to be understood that the features of the numerous examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, novel subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible considering this disclosure. It is intended that the scope of the present disclosure be limited not by this detailed description, but by the claims appended hereto. Future filed applications claiming priority to this application may claim the disclosed subject matter in a different manner and may include any set of one or more features as variously disclosed or otherwise demonstrated herein.

What is claimed is:

1. A controller of a drug delivery system, comprising:
a processor operable to execute programming instructions;
a user interface including a display and user input circuitry;
a memory operable to store the programming instructions; and
a communication circuitry coupled to the processor operable to receive and transmit wireless communication signals, wherein the processor, when executing the programming instructions, is operable to:
  receive an indication that a user is experiencing a sickness;
  based on the indication, adjust one or more settings of a medication delivery algorithm;
  cause delivery of a liquid drug based on the adjusted one or more settings;
evaluate a glucose measurement value with respect to a hyperglycemic threshold;
evaluate a ketone measurement value with respect to a selected ketone level threshold of a plurality of ketone level thresholds; and
  increase a total daily insulin value based on the evaluation of the glucose measurement value and the evaluation of the ketone measurement value.

2. The controller of claim 1, wherein the processor is operable to:
generate a prompt with a list of symptoms of the sickness; and
receive a selection from the user from among the list of symptoms.

3. The controller of claim 1, wherein the processor is operable to:
receive a glucose measurement value from a glucose sensor via the communication circuitry, or
receive a ketone level reading from a ketone sensor via the communication circuitry.

4. The controller of claim 1, wherein the processor, when evaluating the ketone measurement value with respect to the selected ketone level threshold from the plurality of ketone level thresholds, is operable to:
determine whether the ketone measurement value is greater than the selected ketone level threshold; and based on the determination, generate a ketone measurement value indication.

5. The controller of claim 1, wherein the processor is further operable to:
adapting a basal dosage, bolus dosage, and a delivery schedule based on the increased total daily insulin.

6. The controller of claim 5, wherein the processor, when adapting the basal dosage, is operable to:
increase the basal dosage by a selected percentage of a nominal basal dosage setting.

7. The controller of claim 6, wherein the processor, when evaluating the ketone measurement value with respect to the selected ketone level threshold from the plurality of ketone level thresholds, is operable to:
determine whether the ketone measurement value is greater than the selected ketone level threshold; and
based on the determination, generate a ketone measurement value indication.

8. The controller of claim 6, wherein the processor, when adapting the bolus dosage, is operable to:
increase the bolus dosage based on a bolus delivery calculation that utilizes the increased total daily insulin.

9. A controller of a drug delivery system, comprising:
a processor operable to execute programming instructions;
a user interface including a display and user input circuitry;
a memory operable to store the programming instructions; and
a communication circuitry coupled to the processor operable to receive and transmit wireless communication signals, wherein the processor, when executing the programming instructions, is operable to:
receive an indication that a user is experiencing a sickness;
based on the indication, adjust one or more settings of a medication delivery algorithm;
cause delivery of a liquid drug based on the adjusted one or more settings;
evaluate a glucose measurement value with respect to a hypoglycemic threshold range;
evaluate a ketone measurement value with respect to a selected ketone level threshold of a plurality of ketone level thresholds; and
reduce a total daily insulin value based on the evaluation of the glucose measurement value and the evaluation of the ketone measurement value.

* * * * *